United States Patent
Chawla et al.

(10) Patent No.: US 12,215,386 B2
(45) Date of Patent: *Feb. 4, 2025

(54) BLOOD BIOMARKERS FOR APPENDICITIS AND DIAGNOSTICS METHODS USING BIOMARKERS

(71) Applicant: The George Washington University, Washington, DC (US)

(72) Inventors: Lakhmir S. Chawla, McLean, VA (US); Timothy A. McCaffrey, Silver Spring, MD (US)

(73) Assignee: The George Washington University, Washington, DC (US)

( * ) Notice: Subject to any disclaimer, the term of this patent is extended or adjusted under 35 U.S.C. 154(b) by 303 days.

This patent is subject to a terminal disclaimer.

(21) Appl. No.: 17/343,285

(22) Filed: Jun. 9, 2021

(65) Prior Publication Data
US 2022/0090199 A1   Mar. 24, 2022

Related U.S. Application Data

(63) Continuation of application No. 15/521,224, filed as application No. PCT/US2015/057009 on Oct. 22, 2015, now Pat. No. 11,066,706.

(60) Provisional application No. 62/067,414, filed on Oct. 22, 2014.

(51) Int. Cl.
*C12Q 1/68* (2018.01)
*C12Q 1/6883* (2018.01)
*G01N 33/68* (2006.01)
*G01N 33/566* (2006.01)
*G01N 33/84* (2006.01)

(52) U.S. Cl.
CPC ....... *C12Q 1/6883* (2013.01); *G01N 33/6893* (2013.01); *C12Q 2600/158* (2013.01); *G01N 33/566* (2013.01); *G01N 33/84* (2013.01); *G01N 2500/04* (2013.01); *G01N 2800/06* (2013.01)

(58) Field of Classification Search
None
See application file for complete search history.

(56) References Cited

U.S. PATENT DOCUMENTS

| | | |
|---|---|---|
| 2012/0028268 A1 | 2/2012 | Kentsis et al. |
| 2013/0122528 A1 | 5/2013 | Tyrell et al. |
| 2013/0171670 A1 | 7/2013 | Bar-Or |
| 2014/0135225 A1 | 5/2014 | Crow |
| 2014/0220580 A1 | 8/2014 | Brown |

FOREIGN PATENT DOCUMENTS

| | | |
|---|---|---|
| SU | 1446526 A1 | 12/1988 |
| WO | WO-2004/059293 A2 | 7/2004 |
| WO | WO-2016/065202 A1 | 4/2016 |
| WO | WO-2016/065204 A1 | 4/2016 |

OTHER PUBLICATIONS

Haaf et al., "Quantitative determination of rDNA transcription units in vertebrate cells", Exp Cell Res 193 : 78-86 (1991).
Huang et al., "Systematic and integrative analysis of large gene lists using DAVID bioinformatics resources", Nat Protoc 4 : 44-57, (2009).
Huang et al., "The Identification of Novel Proteins That Interact With the GLP-1 Receptor and Restrain its Activity", Mol Endocrinol 27 : 1550-1563, (2013).
Huckins et al., "A novel biomarker panel to rule out acute appendicitis in pediatric patients with abdominal pain", Am J Emerg Med 31 : 1368-1375 (2013).
International Search Report in International Application No. PCT/US2015/057007, dated Jan. 29, 2016.
Jackson et al., "Culture—Independent Evaluation of the Appendix and Rectum Microbiomes in Children with and without Appendicitis", PLoS One, vol. 9, Issue 4, e95414, pp. 1-9 (2014).
Kaya et al., "The Diagnostic Value of D-dimer , Procalcitonin and CRP in Acute Appendicitis", Int J Med Sci 9 : 909-915 (2012).
Keyzer et al., "Acute Appendicitis : Comparison of Low-Dose and Standard-Dose Unenhanced Multi-Detector Row CT", Radiology 232 : 164-172 (2004).
Kim et al., "Acute Appendicitis in Young Adults : Low-versus Standard-Radiation-Dose Contrast-enhanced Abdominal CT for Diagnosis", Radiology 260 : 437-445 (2011).
Kirkil et al., "Appendicitis scores may be useful in reducing the costs of treatment for right lower quadrant pain", Ulus Travma Acil Cerrahi Derg 19 : 13-19 (2013).
Kubo et al., "Analysis of genes induced in peripheral nerve after axotomy using cDNA microarrays", J Neurochem 82 : 1129-1136, (2002).
Memon et al., "Acute appendicitis : Diagnostic accuracy of Alvarado scoring system," Asian J Surg 36 : 144-149 (2013).
Miglioretti et al., "Pediatric Computed Tomography and Associated Radiation Exposure and Estimated Cancer Risk," JAMA Pediatr., 167 : 700-707 (2013).
Murphy et al., "Acute appendicitis is characterized by a uniform and highly selective pattern of inflammatory gene expression", Mucosal Immunology, vol. 1, No. 4, pp. 297-308 (2008).
Ohkusa et al., "Induction of experimental ulcerative colitis by Fusobacterium varium isolated from colonic mucosa of patients with ulcerative colitis", Gut 52 : 79-83 (2003).
Peyyala et al., "Oral microbial biofilm stimulation of epithelial cell responses", Cytokine 58 (1):65-72 (2012).

(Continued)

*Primary Examiner* — Jehanne S Sitton
(74) *Attorney, Agent, or Firm* — BLANK ROME LLP

(57) ABSTRACT

The invention relates to methods and kits for diagnosing and/or treating appendicitis in a subject, comprising obtaining a biological sample rom said subject; detecting RNA expression levels of at least three or more biomarkers in the biological sample and comparing the expression levels of said at least three or more biomarkers to a control sample wherein an increase or decrease in the level of expression of said at least three or more biomarkers as compared to the control sample is indicative of appendicitis.

17 Claims, 7 Drawing Sheets

(56) References Cited

OTHER PUBLICATIONS

Pike et al., "A novel hypothesis for an alkaline phosphatase 'rescue' mechanism in the hepatic acute phase immune response", Biochim Biophys Acta 1832 : 2044-2056 (2013).

Poortinga et al., "C-MYC coordinately regulates ribosomal gene chromatin remodeling and Pol I availability during granulocyte differentiation", Nucleic Acids Res 39 (8) : 3267-3281 (2011).

Poortman et al., "Improving Diagnosis of Acute Appendicitis : Results of a Diagnostic Pathway with Standard Use of Ultrasonography Followed by Selective Use of CT", Journal of the American College of Surgeons 208 (3) : 434-441 (2009).

Ramdass et al., "Association between the appendix and the fecalith in adults," Can J Surg 58 : 10-14 (2015).

Remacha et al., "Ribosomal Acidic Phosphoproteins P1 and P2 Are Not Required for Cell Viability but Regulate the Pattern of Protein Expression in *Saccharomyces cerevisiae*", Mol Cell Biol 15 (9) : 4754-4762 (1995).

Rosen et al., "ACR Appropriateness Criteria® Right Lower Quadrant Pain-Suspected Appendicitis," Journal of the American College of Radiology 8 : 749-755 (2011).

Seetahal et al., "Negative appendectomy : a 10-year review of a nationally representative sample", The American Journal of Surgery, 201 : 433-437 (2011).

Seo et al., "Diagnosis of Acute Appendicitis With Sliding Slab Ray-Sum Interpretation of Low-Dose Unenhanced CT and Standard Dose IV Contrast-Enhanced CT Scans", American Journal of Roentgenology, 193 : 96-105 (2009).

Shiue et al., "Myc-induced anchorage of the rDNA IGS region to nucleolar matrix modulates growth-stimulated changes in higher order rDNA architecture", Nucleic Acids Res 42 : 5505-5517 (2014).

Subrahmanyam et al., "RNA expression patterns change dramatically in human neutrophils exposed to bacteria", Blood 97 : 2457-2468 (2001).

Swidsinski et al., "Acute appendicitis is characterized by local invasion with Fusobacterium nucleatum / necrophorum", Gut 60 : 34-40 (2011).

Teixeira et al., "Appendicitis : changing perspectives", Adv Surg 47 : 119-140 (2013).

Uemura et al., "Overexpression of ribosomal RNA in prostate cancer is common but not linked to rDNA promoter hypomethylation", Oncogene 31 : 1254-1263 (2012).

Wai et al., "The Utility of the Emergency Department Observation Unit for Children With Abdominal Pain", Pediatr Emerg Care 29 : 574-578 (2013).

Watson et al., "Increased prokineticin 2 expression in gut inflammation : role in visceral pain and intestinalion transport", Neurogastroenterol Motil 24 : 65-75 , e12 (2012).

Williams et al., "Distribution of the interleukin-8 receptors , CXCR1 and CXCR2 , in inflamed gut tissue", Journal of Pathology, vol. 192, No. 4 , pp. 533-539 (2000).

Wu et al., "Diagnostic Role of Procalcitonin in Patients with Suspected Appendicitis", World J Surg 36 : 1744-1749 (2012).

Zeillemaker et al., "Peritoneal Interleukin-8 in Acute Appendicitis", J Surg Res 62 : 273-277 (1996).

Zhang et al., "Identification and Analysis of Over 2000 Ribosomal Protein Pseudogenes in the Human Genome" Genome Res 12 : 1466-1482 (2002).

Zhong et al., "Acute appendicitis in children is associated with an abundance of bacteria from the phylum Fusobacteria", J Pediatr Surg 49 : 441-446 (2014).

Chawla et al., "Acute appendicitis : transcript profiling of blood identifies promising biomarkers and potential underlying processes", BMC Medical Genomics, vol. 9, No. 1, pp . 1-11 (Jul. 2016).

Supplementary European Search Report in European Patent Application No. 15853139, dated Jan. 31, 2018.

Supplementary European Search Report in European Patent Application No. 15853565.8, dated Mar. 15, 2018.

International Search Report and Written Opinion in International Application No. PCT/US2015/057009, dated Jan. 4, 2016.

"Platform GPL10558.-Illumina Human HT-12 V4.0 expression beadchip ", Jun. 17, 2010 (Jun. 17, 2010), XP55696201, Retrieved from the Internet : URL : https : // http ://www.ncbi.nlm.nih .gov / geo / query / acc.cgi ? acc = GPL10558.

Ant A, Bharti R, Eves I, Hasler R, Miettinen P, et al., (2013), "Characteristic changes in microbial community composition and expression of innate immune genes in acute appendicitis", Innate Immunity 2015, vol. 21 (1), 30-41.

Asare, Adam L. et al., "Differential gene expression profiles are dependent upon method of peripheral blood collection and RNA isolation", BMC Genomics, 2008, 9 : 474, pp. 1-10.

Communication pursuant to Rule 94 (3) EPC in Application No. 15, 853 139.2 dated May 26, 2020, 9 pages.

Data Sheet : Gene Expression Array-Based Gene Expression Analysis, illlumina, Jan. 1, 2011, (Jan. 1, 2011), XP055259707, Retrieved from the Internet : URL : http ://support.illumina.com/content/dam/ illumina-marketing / documents / products / datasheets / datasheetgene_ exp_analysis.pdf.

Derenzini, M. et al., "Spatial Redistribution of Ribosomal Chromatin in the Fibrillar Centres of Human Circulating Lymphocytes after Stimulation of Transcription", Experimental Cell Research, 170 (1987), 31-41.

Giannini, Elisa et al., "The chemokineBv8 / prokineticin 2 is up regulated in inflammatory granulocytes and modulates inflammatory pain", PNAS, Aug. 25, 2009, vol. 106, No. 34, 14646-14651.

Huang et al, "Determination of plasma beta-defensin-3 concentration in patients with acute appendicitis and its clinical significnce", Fangshe Mianyxue Zazhi, vol. 25, No. 6, Jan. 1, 2012 (Jan. 1, 2012), pp. 665-666, XP055696334.

Li et al, "Determination of plasma beta-defensin-2 concentration in patients with acute appendicitis and its clinical significance", Fangshe Mianyixue Zazhi, vol. 25, No. 1, Jan. 1, 2012 (Jan. 1, 2012), pp. 47-48, XP055696332.

Miglioretti DL, Johnson E, Williams A, Greenlee RT, Weinmann S, et al., (2013), "The use of computed tomography in pediatrics and the associated radiation exposure and estimated cancer risk", JAMA Pediatr 167 : 700-707.

Odani, Toshio et al., "Up-regulated expression of HLA-DRB5 transcripts and high frequency of the HLA-DRB5 * 01 : 05 allele inscleroderma patients with interstitial lung disease", Rheumatology, 2012,51 : 1765-1774doi : 10.1093 /rheumatology/kes149, Advance Access publication, Jun. 20, 2012.

Ohkusa T, Okayasu I, Ogihara T, Morita K, Ogawa M, et al., (2003), Induction of experimental ulcerative colitis by Fusobacterium varium isolated from colonic mucosa of patients with ulcerative colitis, Gut 52 : 79-83.

Palmer, Chana et al., "Cell-type specific gene expression profiles of leukocytes in human peripheral blood", BMC Genomics, 2006, 7 : 115, doi : 10.1186 / 1471-2164-7-115.

Rudkowska et al; FASEB, vol. 25, No. 1, supplement, Apr. 2011, from the internet pp. 1-3.

Ahn, "LOCAT (low-dose computed tomography for appendicitis trial) comparing clinical outcomes following low- vs standard-dose computed tomography as the first-line imaging test in adolescents and young adults with suspected acute appendicitis : study protocol for a randomized controlled trial", Trials 15 : 28, pp. 1-10 (2014).

Andersson et al., "Can new inflammatory markers improve the diagnosis of acute appendicitis", World J Surg 38 : 2777-2783, (2014).

Arlt et al., "Characteristic changes in microbial community composition and expression of innate immune genes in acute appendicitis", Innate Immun, vol. 21 (1) : pp . 310-41, (2015).

Baines et al., "Sputum gene expression signature of 6 biomarkers discriminates asthma inflammatory phenotypes," J Allergy Clin Immunol 133 : 997-1007 (2014).

Bhuiya et al., "Emergency Department Visits for Chest Pain and Abdominal Pain : United States, 1999-2008", NCHS Data Brief, 43, pp. 1-8 (2010).

Charfi et al, "Histopathological findings in appendectomy specimens : a study of 24,697 cases", Int J Colorectal Dis 29 : 1009-1012 (2014).

(56) References Cited

OTHER PUBLICATIONS

Collins et al., "The accuracy of pre-appendectomy computed tomography with histopathological correlation : a clinical audit , case discussion and evaluation of the literature", Emerg Radiol 21 : 589-595 (2014).

Congiu et al., "Expression of common housekeeping genes is affected by disease in human hepatitis C virus-infected liver", Liver Int 31 : 386-390 (2011).

D'Souza et al., "Bilirubin ; a diagnostic marker for appendicitis", Int J Surg 11 : 1114-1117 (2013).

Drake et al., "Progress in the Diagnosis of Appendicitis : A Report from Washington State's Surgical Care and Outcomes Assessment Program", Ann Surg 256 : 586-594 (2012).

Guinane et al., "Microbial Composition of Human Appendices from Patients Following Appendectomy", MBio , vol. 4, Issue 1, e0036612, pp. 1-6 (2013).

European Office Action, Application No. 19 153 228.2, dated Jul. 6, 2021.

Greenbaum D. et al: "Comparing Protein Abundance and MRNA Expression Levels on a Genomic Scale," Genome Biology (Online), Biomed Central Ltd, GB, vol. 40, No. 9, Jan. 1, 2003 (Jan. 1, 2003,) pp. 117.01-117.08.

Kim et al., "Acute Appendicitis in Young Adults: Low- versus Standard-Radiation-Dose Contrast-enhanced Abdominal CT for Diagnosis", Radiology (2011), vol. 260, pp. 437-445.

Poortman et al., "Improving Diagnosis of Acute Appendicitis: Results of a Diagnostic Pathway with Standard Use of Ultrasonography Followed by Selective Use of CT", Journal of the American College of Surgeons (2009), vol. 208, pp. 434-441.

Seetahal et al., "Negative appendectomy: a 10-year review of a nationally representative sample", The American Journal of Surgery (2011), vol. 201, pp. 433-437.

Shiue et al., "Myc-induced anchorage of the rDNA IGS region to nucleolar matrix modulates growth-stimulated changes in higher-order rDNA architecture", Nucleic Acids Res (2014), vol. 42, pp. 5505-5517.

Yamaguchi (2009;58: 192-7).

Kanmura et al (Inflam Bowel Dis, 2009;vol. 15, No. 6 p. 909-917).

Grupp et al. (peritoneal Dialysis International vol. 27. pp. 654-662).

Weirong et al. (Fangshe Mianyixue Zazhi 2012;25(6),655-666 Abstract).

Wuyts, Anjaet al., Characterization of Synthetic Human Granulocyte Chemotactic Protein 2:Usage of Chemokine Receptors CXCR1 and CXCR2 and in Vivo Inflammatory Properties,Biochemistry1997, 36, 2716-2723.

Rudkowska, Iwona, et al. "Effects of n-3 polyunsaturated fatty acids and peroxisome proliferator-activated receptor alpha on low-density lipoprotein particle size." (2011): 782-4.

Rudkowska, Iwona, et al. "Gene expression and pathway changes after n-3 PUFA supplementation in healthy subjects." (2011): 599-4. Abstract only; 2 pages.

BLOOD BIOMARKERS FOR APPENDICITIS AND DIAGNOSTICS METHODS USING BIOMARKERS

CROSS-REFERENCE OF RELATED APPLICATION

This application is a Continuation Application of U.S. patent application Ser. No. 15/521,224, now U.S. patent Ser. No. 11/066,706, filed on Apr. 21, 2017, which is based on National Stage Entry of International Application PCT/US2015/057009, filed on Oct. 22, 2015, which claims priority to U.S. Provisional application 62/067,414, filed on Oct. 22, 2014, each of which is entirely incorporated herein by reference in their entirety.

BACKGROUND

Technical Field

The field of the currently claimed embodiments of this invention relate to methods and kits for assessing and treating abdominal discomfort/pain (the terms abdominal pain and abdominal discomfort will be used interchangeably throughout) and appendicitis in a subject, and more particularly to assessing and treating abdominal discomfort and appendicitis in a subject using the analysis of biomarkers isolated from the subject.

Discussion of Related Art

Abdominal pain is a major cause of hospital visits, accounting for about 10% of 62 million visits per year by adults who present at an emergency department (ED) for non-injury causes [1]. Acute appendicitis is one of the most common causes of abdominal pain and results in nearly 750,000 ED visits with approximately 250,000 appendectomies performed annually. Globally, a small but significant portion of the operations are "negative appendectomies", resulting in the removal of a non-inflamed appendix due to misdiagnosis [2-4], reported as high as 17-28% outside the US and Western Europe [5,6].

Prior to the widespread availability of computed tomography (CT) scans, the accurate diagnosis of appendicitis could be challenging, and in places where CT is still not available, the Alvarado score of clinical characteristics is a widely used diagnostic tool [5,6]. Currently in the United States, CT scanning is the 'gold standard' for the diagnosis of appendicitis, with magnetic resonance imaging (MRI) being a reasonable alternative in pregnant women [7], and ultrasound sonography being an acceptable alternative for preliminary diagnostics to avoid radiation [8]. While CT is the most sensitive and specific diagnostic tool for appendicitis [9,10], and used in almost 98% of patients undergoing appendectomy in the US [11], CT scanning carries a significant radiation exposure, and epidemiologic data suggest that radiation exposure can increase the risk of developing a future malignancy [12]. This issue is of particular concern in children because they are more sensitive to the hazards of radiation, they are among the most common patients to present to the ED with abdominal pain, and have the highest rate of misdiagnosis [10,13]. In an attempt to reduce the damaging effect of CT scans, several clinical trials are examining the diagnostic utility of lower doses of radiation, primarily in children [14-16].

In order to utilize CT scanning more appropriately, and to improve diagnosis in areas where CT scans are unavailable, blood biomarkers were identified that serve as a preliminary safe and rapid test to help identify patients with appendicitis. Genome-wide profiling of RNA transcripts in whole blood RNA of patients presenting at the ED for abdominal pain was conducted, resulting in confirmed appendicitis versus other abdominal abnormalities.

Some embodiments of the present invention include methods and kits for assessing and treating abdominal discomfort and appendicitis in a subject, and more particularly to assessing and treating abdominal discomfort and appendicitis in a subject using the analysis of biomarkers isolated from the subject.

SUMMARY

Embodiments of the invention include methods of diagnosing appendicitis in a subject, comprising obtaining a biological sample from said subject; detecting expression levels of at least three or more biomarkers in the biological sample selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; and comparing the expression levels of said at least three or more biomarkers to a control sample wherein an increase or decrease in the level of expression of said at least three or more biomarkers as compared to the control sample is indicative of appendicitis.

Embodiments of the invention include methods of treating appendicitis in a subject, comprising: obtaining a biological sample from said subject; detecting expression levels of at least three or more biomarkers in the biological sample selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; comparing the expression levels of said at least three or more biomarkers to a control sample wherein an increase or decrease in the level of expression of said at least three or more biomarkers as compared to the control sample is indicative of appendicitis; and treating the subject for appendicitis.

Embodiments of the invention include kits for use in diagnosing appendicitis in a subject comprising: agents that specifically bind at least three or more biomarkers selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; a container for housing said agents; and instructions for use of the agents for determining expression levels of said at least three or more biomarkers and for comparing said expression levels to a control sample wherein an increase or decrease in the expression levels of said at least three or more biomarkers as compared to the control sample is indicative of and methods of using such kits for the diagnosis and/or treatment of appendicitis.

Embodiments of the invention include systems for evaluating biomarker levels, comprising a plurality of reagents which specifically bind for detection a plurality of biomarkers selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; an assay instrument configured to (i) receive a biological sample, (ii) contact the plurality of reagents with the biological sample and (iii) generate and quantitatively display in human readable form one or more assay results indicative of binding of each biomarker which is assayed to a respective specific binding reagent in the plurality of reagents.

BRIEF DESCRIPTION OF THE DRAWINGS

Further objectives and advantages will become apparent from a consideration of the description, drawings, and examples.

DETAILED DESCRIPTION

Figure 1:
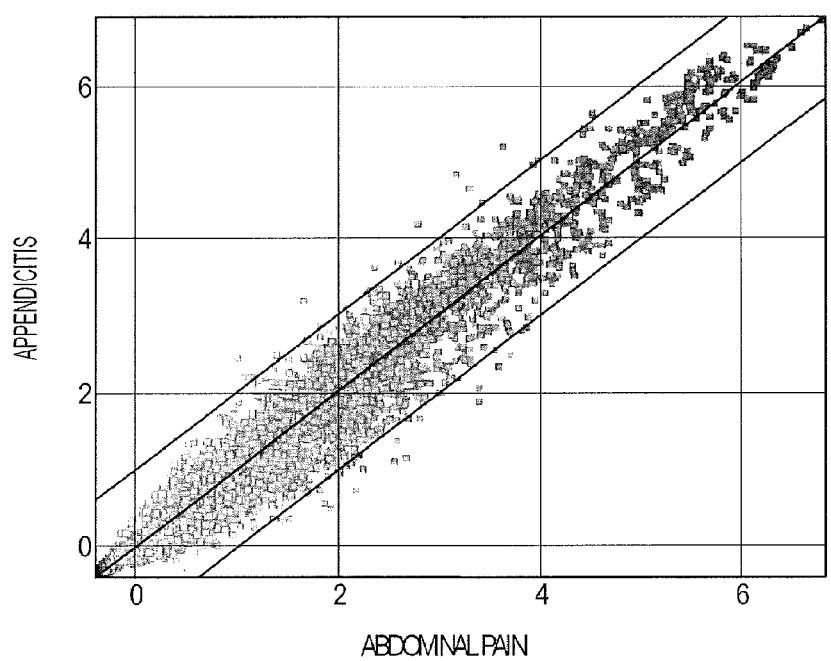
FIG. 1 is a scatterplot of the expression patterns in 2 groups of patients.

In some embodiments, the invention relates to a method of diagnosing appendicitis in a subject, comprising obtaining a biological sample from said subject; detecting expression levels of at least three or more biomarkers in the biological sample selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; and comparing the expression levels of said at least three or more biomarkers to a control sample wherein an increase or decrease in the level of expression of said at least three or more biomarkers as compared to the control sample is indicative of appendicitis.

In some embodiments, the invention relates to the method above, wherein the biological sample is a blood or serum sample.

In some embodiments, the invention relates to the method above, wherein the at least three biological samples are selected from the list consisting of Interleukin 8 receptor β, Defensin alpha 1, Defensin alpha 1B, Defensin alpha 3 and Alkaline phosphatase.

In some embodiments, the invention relates to a method of diagnosing appendicitis as above, and further comprising determining the ratio of expression between Alkaline phosphatase or Interleukin 8 receptor β and Defensin alpha 1, Defensin alpha 1B or Defensin alpha 3 and comparing said ratio to a control sample, wherein an increase in the ratio of expression is indicative of appendicitis.

In some embodiments, the invention relates to the method above, wherein the detecting expression levels of at least three or more biomarkers comprises measuring RNA levels of said at least three or more biomarkers.

In some embodiments, the invention relates to the method above, wherein measuring RNA levels comprises using reverse transcriptase and polymerase chain reaction.

In some embodiments, the invention relates to the method above, wherein measuring RNA levels comprises using microarray analysis.

In some embodiments, the invention relates to the method above, wherein measuring RNA levels comprises using RNA sequencing.

In some embodiments, the invention relates to the method above, wherein comparing the expression levels of said at least three or more biomarkers comprises using a prediction model to determine if a pattern of expression of said at least three or more biomarkers is indicative of appendicitis.

In some embodiments, the invention relates to the method above by assigning a likelihood of a future outcome to a subject diagnosed with appendicitis.

In some embodiments, the invention relates to the method above, wherein the future outcome of the subject is mortality.

In some embodiments, the invention relates to the method above, wherein the subject is being evaluated for abdominal pain.

In some embodiments, the invention relates to a method of treating appendicitis in a subject, comprising: obtaining a biological sample from said subject; detecting expression levels of at least three or more biomarkers in the biological sample selected from the group consisting of Chemokine C-X-C receptor 1, Interleukin 8 receptor β, Fc frag of IgG receptor IIIb (CD16b), MIIC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein 123, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; comparing the expression levels of said at least three or more biomarkers to a control sample wherein an increase or decrease in the level of expression of said at least three or more biomarkers as compared to the control sample is indicative of appendicitis; and treating the subject for appendicitis.

In some embodiments, the invention relates to the method of treating appendicitis above, wherein treating the subject for appendicitis comprises administering antibiotics to said subject, removing said subject's appendix or a combination thereof.

In some embodiments, the invention relates to the method of treating appendicitis above, wherein the biological sample is a blood or serum sample.

In some embodiments, the invention relates to the method of treating appendicitis above, wherein the at least three biological samples are selected from the list consisting of Interleukin 8 receptor β, Defensin alpha 1, Defensin alpha 1B, Defensin alpha 3 and Alkaline phosphatase.

In some embodiments, the invention relates to a method of treating appendicitis as above, and further comprises determining the ratio of expression between Alkaline phosphatase or Interleukin 8 receptor β and Defensin, alpha 1, Defensin, alpha 1B or Defensin, alpha 3 and comparing said ratio to a control sample, wherein an increase in the ratio of expression is indicative of appendicitis.

In some embodiments, the invention relates to the method of treating appendicitis above, wherein detecting expression levels of at least three or more biomarkers comprises measuring RNA levels of said at least three or more biomarkers.

In some embodiments, the invention relates to the method of treating appendicitis above, wherein measuring RNA levels comprises using reverse transcriptase and polymerase chain reaction.

In some embodiments, the invention relates to the method of treating appendicitis above, wherein measuring RNA levels comprises using microarray analysis.

In some embodiments, the invention relates to the method of treating appendicitis above, wherein measuring RNA levels comprises using RNA sequencing.

In some embodiments, the invention relates to the method of treating appendicitis above, wherein comparing the expression levels of said at least three or more biomarkers comprises using a prediction model to determine if a pattern of expression of said at least three or more biomarkers is indicative of appendicitis.

In some embodiments, the invention relates to the method of treating appendicitis above and further comprises performing a computed tomography scan on the subject prior to treating the subject for appendicitis.

In some embodiments, the invention relates to a kit for use in diagnosing appendicitis in a subject comprising: agents that specifically bind at least three or more biomarkers selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; a container for housing said agents; and instructions for use of the agents for determining expression levels of said at least three or more biomarkers and for comparing said expression levels to a control sample wherein an increase or decrease in the expression levels of said at least three or more biomarkers as compared to the control sample is indicative of.

In some embodiments, the invention relates to the kit above, wherein the agents are polynucleotides that specifically bind to RNA transcripts of the at least three or more biomarkers.

In some embodiments, the invention relates to the kit above, wherein the polynucleotides are labeled with a detectable marker.

In some embodiments, the invention relates to the kit above, wherein the agents are polynucleotides that amplify polynucleotides encoding the at least three or more biomarkers.

In some embodiments, the invention relates to the kit above, wherein the agents that specifically bind to at least three or more biomarkers bind to at least three or more biomarkers selected from the list consisting of Interleukin 8 receptor β, Defensin alpha 1, Defensin alpha 1B, Defensin alpha 3 and Alkaline phosphatase.

In some embodiments, the invention relates to the kit above, wherein the kit further comprises instructions for determining the ratio of expression between Alkaline phosphatase or Interleukin 8 receptor β and Defensin, alpha 1, Defensin, alpha 1B or Defensin, alpha 3 and comparing said ratio to a control sample, wherein an increase in the ratio of expression is indicative of appendicitis.

In some embodiments, the invention relates to the kit above, wherein the kit further comprises reagents for reverse transcriptase and polymerase chain reaction.

In some embodiments, the invention relates to the kit above, wherein the kit further comprises reagents for microarray analysis.

In some embodiments, the invention relates to the kit above, wherein the kit further comprises reagents for RNA sequencing.

In some embodiments, the invention relates to the kit above, wherein the instructions included with the kit further comprise instructions for comparing the expression levels of said at least three or more biomarkers by using a prediction model to determine if a pattern of expression of said at least three or more biomarkers is indicative of appendicitis.

In some embodiments, the invention relates to a method of diagnosing appendicitis in a subject comprising: obtaining a biological sample from said subject; and contacting the biological sample from said subject with the kit above.

In some embodiments, the invention relates to a method of treating appendicitis in a subject comprising: obtaining a biological sample from said subject; contacting the biological sample from said subject with the kit above; and treating the subject for appendicitis by administering antibiotics to said subject, removing said subject's appendix or a combination thereof.

In some embodiments, the invention relates to a system for evaluating biomarker levels, comprising a plurality of reagents which specifically bind for detection a plurality of biomarkers selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; an assay instrument configured to (i) receive a biological sample, (ii) contact the plurality of reagents with the biological sample and (iii) generate and quantitatively display in human readable form one or more assay results indicative of binding of each biomarker which is assayed to a respective specific binding reagent in the plurality of reagents.

In some embodiments, the invention relates to the system above, wherein the reagents comprise a plurality of antibodies, at least one of which binds to each of the biomarkers which are assayed.

In some embodiments, the invention relates to the system above, wherein assay instrument comprises an assay device and an assay device reader, wherein the plurality of antibodies are immobilized at a plurality of predetermined locations within the assay device, wherein the assay device is configured to receive the biological sample such that the biological sample contacts the plurality of predetermined locations, and wherein the assay device reader interrogates the plurality of predetermined locations to generate the assay results.

Definitions

To facilitate an understanding of the present invention, a number of terms and phrases are defined below.

As used herein, the singular forms "a", "an", and "the" include plural forms unless the context clearly dictates otherwise. Thus, for example, reference to "a binding agent" includes reference to more than one binding agent.

The terms "diagnostic" and "diagnosis" refer to identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g., when positive assay results are obtained). In the latter context, "detecting" and "diagnosing" are considered synonymous.

The terms "subject", "patient" or "individual" generally refer to a human, although the methods of the invention are not limited to humans, and should be useful in other mammals (e.g., cats, dogs, etc.).

"Sample" is used herein in its broadest sense. A sample may comprise a bodily fluid including blood, serum, plasma, tears, aqueous and vitreous humor, spinal fluid, urine, and saliva; a soluble fraction of a cell or tissue preparation, or media in which cells were grown. Means of obtaining suitable biological samples are known to those of skill in the art.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, hybrid antibodies, fusion proteins comprising an antibody portion, and any other modified immunoglobulin molecule comprising an antigen recognition site so long as the antibodies exhibit the desired biological activity. An antibody may be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies may be naked or conjugated to other molecules such as toxins, radioisotopes, etc.

The term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

"Hybrid antibodies" are immunoglobulin molecules in which pairs of heavy and light chains from antibodies with different antigenic determinant regions are assembled together so that two different epitopes or two different antigens may be recognized and bound by the resulting tetramer.

"Isolated" in regard to cells, refers to a cell that is removed from its natural environment and that is isolated or separated, and is at least about 30%, 50%, 75%, and 90% free from other cells with which it is naturally present, but which lack the marker based on which the cells were isolated.

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for a biomarker of interest. Alternatively, the kit can comprise a mass spectrometry (MS) probe. The kit can also include containers containing nucleotide(s) for amplification or silencing of a target nucleic acid sequence, and/or a container comprising a reporter means, such as a biotin-binding protein, e.g., avidin or streptavidin, bound to a detectable label, e.g., an enzymatic, florescent, or radioisotope label. The kit can include all or part of the amino acid sequence of the biomarker, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

Polynucleotides may be prepared using any of a variety of techniques known in the art. The polynucleotide sequences selected as probes (and bind to the biomarkers of interest) should be sufficiently long and sufficiently unambiguous that false positives are minimized. The polynucleotide is preferably labeled such that it can be detected upon hybridization to DNA and/or RNA in the assay being screened. Methods of labeling are well known in the art, and include the use of radiolabels, such as 32P-labeled ATP, biotinylation, fluorescent groups or enzyme labeling. Hybridization conditions, including moderate stringency and high stringency, are well known in the art.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis. Alternatively, RNA molecules may be generated by in vitro or in vivo. Certain portions may be used to prepare an encoded polypeptide.

Any polynucleotide may be further modified to increase stability in vivo and/or in vitro for improved activity and/or storage. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotides and/or antibodies specific to biomarkers of interest can be conjugated to detectable markers to a second molecule. Suitable detectable markers include, but are not limited to, a radioisotope, a fluorescent compound, a bioluminescent compound, chemiluminescent compound, a metal chelator or an enzyme. A second molecule for conjugation can be selected in accordance with the intended use. For example, for therapeutic use, the second molecule can be a toxin or therapeutic agent. Further, bi-specific antibodies specific for two or more biomarkers may be generated using methods generally known in the art. Homodimeric antibodies may also be generated by cross-linking techniques known in the art.

EXAMPLES

The following examples help explain some concepts of the current invention. However, the general concepts of the current invention are not limited to the particular examples.

Example 1: Acute Appendicitis: Transcript Profiling of Blood Identifies Promising Biomarkers and Potential Underlying Processes Materials and Methods Subjects.
Ethics statement: The protocol of this observational study was approved by the Institutional Review Board of The George Washington University, and all subjects gave informed consent. From a cohort of 270 patients presenting to the ED for various reasons, a subset of 40 subjects with a principal complaint of abdominal pain, and who met inclusion/exclusion criteria, were identified, and divided into a discovery set of 20 patients, and a validation set of 20 patients for transcript profiling of whole blood RNA by microarray.

Discovery Set: For the discovery set, we employed 20 subjects who presented to the ED who were undergoing CT scanning. In order to meet criteria, the patient undergoing the CT scan must have had appendicitis suspected in the differential diagnosis. Appendicitis Patients: Patients with appendicitis were diagnosed by CT scanning (n=11), and had research blood samples drawn by venipuncture after anesthetic induction, but prior to skin incision for appendectomy. All cases of appendicitis were confirmed by intraoperative findings and pathology of the removed appendix. Control Patients: Patients included in the control arm (n=9) were patients who were found not to have appendicitis, by both CT scanning and clinical follow-up. This included patients with reported abdominal pain, later found to be caused by diverticulitis, or other gastrointestinal pathologies, but not clinically associated with appendicitis. Blood was drawn at study enrollment for these patients.

Validation Set: Control Patients. Because appendicitis can involve infection, we enrolled 5 patients with lower respiratory tract infections (LRI) in the ED as an 'infection' control. Also, as a control for surgical factors, we enrolled 5 patients undergoing elective ventral hernia or inguinal hernia repair (HER), and these were compared with 10 new patients with surgically confirmed appendicitis (APP). In all surgical patients, including appendicitis and hernia repairs, research blood samples were drawn by venipuncture after anesthetic induction, and prior to skin incision. Two patients, (1 HER, 1 APP) were excluded due to technical complications in RNA purification or microarray analysis.
Blood Samples.
Blood was drawn in 3.2% sodium citrate tubes for frozen plasma samples, in Tempus Blood RNA tubes (ABI) for genome-wide RNA profiling, and in BD Vacutainer K2 tubes for complete blood counts with differentials.
RNA Purification for Transcript Profiling.
Tempus Blood RNA preservation tubes were stored at −80' C and then thawed at 3° C. prior to processing according to manufacturer's methods. Total RNA was purified from whole blood using Tempus Blood RNA kit (ABI), followed by an aggressive DNAsc treatment. Briefly, the preserved whole blood was pelleted at 3000×g for 30 minutes in a 4° C. refrigerated centrifuge, redissolved in lysis buffer and nucleic acids were bound to a column. After washing, nucleic acids were eluted with RNAse/DNAse free water and quantified by with NanoDrop ND-1000 spectrophotometer. DNA was eliminated by aggressive DNAse treatment (TurboDNAse, Ambion) at 2 U/10 µg nucleic acids, followed by affinity removal of the DNAse. The remaining RNA was quantified and RNA integrity was evaluated by 260/280 ratio on ND-1000 and by capillary electrophoresis on a Bioanalyzer 2100 (Agilent). RIN scores>7 were considered acceptable for further sample processing and did not differ between groups.

Microarray Expression Profiling and Analysis.

Purified RNA (100 ng) was labeled with the Illumina cRNA synthesis kit and hybridized to Illumina Human HT-12v4 Expression BeadChip arrays (http://www.illumina.com/products/humanht_12_expression_beadchip_kits_v4.html) containing more than 47,000 probes derived from the NCBI RefSeq release 38 (http://www.ncbi.nlm.nih.gov/refseq/. The arrays were washed and then fluorescence was quantitated on an Illumina HiScan (http://www.illumina.com/systems/hiscan.html).

The fluorescence levels per bead were converted to transcript levels using Illumina GeneStudio, which averaged typically 30 beads per transcript to produce a mean expression level for each of the 46K transcripts. Raw BeadChip fluorescence values were imported into GeneSpring GX12.5 with normalization to the 75-percentile of expression, but without baseline transformation. The main effect of identifying differentially expressed genes (DEG) with respect to appendicitis versus controls was achieved by a combined filter for a p value<0.05 on t test without correction for multiple testing, and 2) fold change>2.0. The DEG list was further analyzed for gene ontologies using DAVID [17]. Using the DEG list, a partial least squares discriminant (PLSD) prediction model was built in GeneSpring and internally validated with a Leave One Out Cross Validation (LOOCV) algorithm. The PLSD model was externally tested by applying the algorithm to a separate validation set of microarray samples not involved in building the model.

The PLSD model described here can be replicated by one of ordinary skill in the art by entering the PLSD loading weights for the genes disclosed in Tables 2 and 3 (below) into a suitable statistical package; in the instant invention, GeneSpring GX13 (Agilent) was used (http://www.genomics.agilent.com/en/product.jsp?cid=AG-PT-130&tabId=AG-PR-1061&_requestid=163669). Tables 5A and 5B below summarizes the loading weights for the genes of Table 2 and Table 3.

Results

Clinical Parameters.

As shown in Table 1, the clinical parameters between patients presenting with appendicitis versus other abdominal indications in the discovery set were generally similar. Age, gender, and body mass index (BMI) were comparable, although the appendicitis patients were principally of Caucasian race. Notably, white blood cell (WBC) counts were comparable, but appendicitis patients had 10% higher neutrophil count that was not statistically significant (77.18% vs 70%, NS). Appendicitis patients had significantly lower blood creatinine level (0.78 vs 1.54 mg/dL, p=0.03 uncorrected). The two groups did not yield significantly different RNA quantities from blood, and the amplification of RNA for microarray labeling was similar.

TABLE 1

Clinical Parameters of Discovery Set

| | | | Appy (11) | ABD (9) |
|---|---|---|---|---|
| Gender | | % male | 55.00 | 55 |
| Age | Mean | Years | 40.73 | 45.89 |
| | SD | | 15.45 | 15.54 |
| BMI | Mean | | 24.51 | 26.44 |
| | SD | | 4.92 | 4.48 |
| Race | | % White | 100.00 | 55.56 |
| | | % Black | 0.00 | 44.44 |
| Smoker | | % | 18.18 | 11.11 |
| Duration of Symptom | Mean | Hours | 29.45 | 32.75 |
| | SD | | 18.68 | 30.65 |
| Temperature | Mean | Celsius | 36.97 | 36.8 |
| | SD | | 0.47 | 0.38 |
| WBC | Mean | K/ul | 13.06 | 13.23 |
| | SD | | 6.44 | 30.65 |
| Elevated Neutrophils | >75% | % | 55.00 | 37.5 |
| Neutrophils | Mean | % WBC | 77.18 | 70 |
| | SD | | 8.76 | 10.14 |
| Creatinine | Mean | | 0.78 | 1.54 |
| | SD | | 0.13 | 1.06 |
| pH | <7.35 | % | 0.00 | 11.11 |
| Na < 130 | | % | 0.00 | 0.00 |
| HCT < 30 | | % | 0.00 | 11.11 |
| Glu > 250 | | % | 0.00 | 0.00 |
| BUN > 30 | | % | 0.00 | 0.00 |
| Immunosupressed | | % | 0 | 0 |
| Steroids | | % | 0 | 0 |
| Antibiotic use | | % | 0 | 0 |
| Oral Rehydration Therapy | Mean | % | 35.60 | ND |
| | SD | | 10.74 | ND |
| Cirrhosis | | % | 0 | 0 |
| Cancer | | % | 0 | 0 |
| Total RNA conc. | Mean | ng/ul | 102.36 | 66.48 |
| | SD | | 72.49 | 34.06 |
| Folds amp. | Mean | Fold | 67.96 | 64.13 |
| | SD | | 60.48 | 35.81 |
| Defensin Score | Mean | RNA level | 1.26 | 2.62* |
| | SD | | 0.92 | 1.46 |

*indicates p < 0.05 (uncorrected probability)
% indicates the percent of patients exhibiting that trait, unless otherwise indicated Identification of RNA Biomarkers for Appendicitis in Whole Blood.

A scatterplot of the expression patterns in the 2 groups (FIG. 1) suggested that there was excellent linearity of quantitation over roughly 7 log 2 orders of magnitude, with globins being the most highly and identically expressed transcripts between groups. By comparing the expression profiles of the two groups, and filtering for both a t-test probability<0.05 and a fold-change of >2.0, 37 transcripts were identified as significantly differentially expressed (Table 2, above). Hierarchical clustering of the 37 DEG was conducted to observe the pattern of covariance of the transcripts in these patients. A heatmap of the expression of these 37 transcripts across all 20 patients in the discovery set is shown in FIG. 2.

FIG. 1 shows a scatterplot of transcript levels in patients with appendicitis. In FIG. 1, whole blood RNA from patients with acute, surgically confirmed appendicitis (n=11) or abdominal pain (n=9) was profiled for the expression level of 45,966 transcripts on Illumina BeadChip Arrays (12v4). The expression level of each transcript was averaged within groups and plotted on a log 2 scale to reveal transcripts which differ between more than 2-fold between groups (outside parallel lines).

Figure 2:
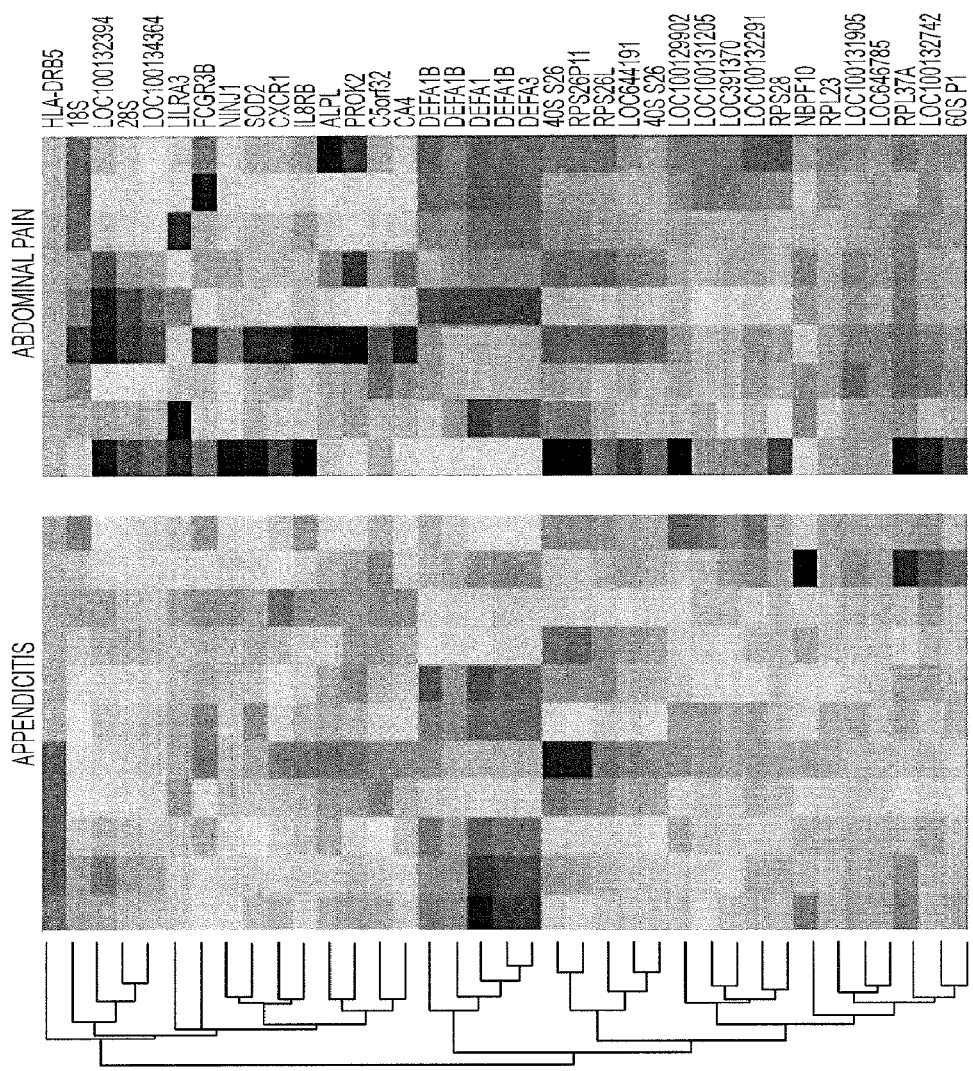
FIG. 2 shows hierarchical clustering of 37 differentially expressed genes in appendicitis patients.
Figure 6:
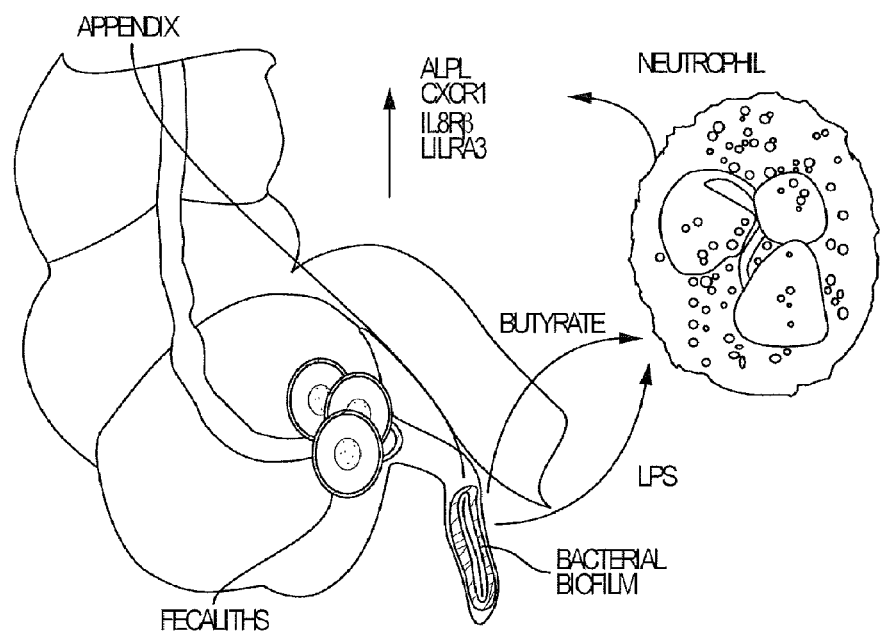
FIG. 6 shows a schematic of a model of appendicitis biomarker pathophysiology.

FIG. 2 shows hierarchical clustering of 37 differentially expressed genes in appendicitis patients. In FIG. 6, transcripts which differed between groups by >2-fold with a t-test probability of <0.05 (uncorrected) were identified by combined filtering. Following a per-gene normalization, DEGs were subjected to hierarchical clustering to identify patterns of covariance among the transcripts. The upper block of transcripts from HLA-DRB5 to CA4 are relatively higher in APP patients (red) compared to patients with other types of abdominal pain (yellow to blue). Conversely, transcripts from defensins (DEFA) and ribosomal transcripts, were relatively lower in APP than abdominal pain patients.

TABLE 2

Differentially expressed genes (DEG) sorted by functional grouping

| Probe ID | p Val | Fold Change | | Expression Level | | DEFINITION | SYMBOL |
|---|---|---|---|---|---|---|---|
| | | | | ABDOM | APPDX | | |
| CHEMOKINES and IMMUNE-RELATED | | | | | | | |
| 3440669 | 0.008 | 2.02 | ↑ | 1.85 | 2.86 | Chemokine C-X-C receptor 1 | CXCR1 |
| 2900327 | 0.003 | 2.59 | ↑ | 2.80 | 4.17 | Interleukin 8 receptor, β (CXCR2) | IL8RB |
| 1450139 | 0.004 | 3.07 | ↑ | 3.17 | 4.79 | Fc frag of IgG receptor IIIb (CD16b) | FCGR3B |
| 6370315 | 0.017 | 3.16 | ↑ | −0.11 | 1.55 | MHC class II, DR beta 5 | HLA-DRB5 |
| 6110037 | 0.007 | 2.36 | ↑ | 2.38 | 3.62 | Leukocyte IgG-like receptor A3 | LILRA3 |
| DEFENSINS | | | | | | | |
| 4540239 | 0.019 | 2.80 | ↓ | 3.39 | 1.91 | Defensin, alpha 1 | DEFA1 |
| 870477 | 0.024 | 2.29 | ↓ | 2.60 | 1.40 | Defensin, alpha 1B (3 probesets) | DEFA1B |
| 2970747 | 0.017 | 2.69 | ↓ | 2.58 | 1.15 | Defensin, alpha 3, neutrophil-spec. | DEFA3 |
| TRANSLATION and PROTEIN SYNTHESIS | | | | | | | |
| 3180609 | 0.002 | 2.69 | ↑ | 1.04 | 2.47 | 18S ribosomal RNA, non-coding | 18S rRNA |
| 6280504 | 0.005 | 2.05 | ↑ | 1.20 | 2.23 | 28S ribosomal RNA, non-coding | 28S rRNA |
| 3190348 | 0.007 | 2.01 | ↓ | 2.16 | 1.15 | 60S acidic ribosomal protein P1 | RPLP1 |
| 6270307 | 0.006 | 2.04 | ↓ | 2.04 | 1.01 | 40S ribosomal protein S26 (3 sets) | RPS26 |
| 380575 | 0.000 | 2.14 | ↓ | 1.49 | 0.39 | Ribosomal protein L23 | RPL23 |
| 990273 | 0.012 | 2.48 | ↓ | 3.39 | 2.08 | Ribosomal protein L37a | RPL37A |
| 650349 | 0.008 | 2.00 | ↓ | 2.20 | 1.19 | Ribosomal protein S28 | RPS28 |
| STRESS and INJURY RELATED | | | | | | | |
| 6100356 | 0.002 | 2.84 | ↑ | 3.63 | 5.14 | Alkaline phosphatase, liver/bone | ALPL |
| 6380672 | 0.001 | 2.11 | ↑ | 1.42 | 2.50 | Carbonic anhydrase IV | CA4 |
| 1510681 | 0.012 | 2.01 | ↓ | 3.56 | 2.55 | Neuroblastoma breakpt family 10 | NBPF10 |
| 7380706 | 0.001 | 2.10 | ↑ | 2.61 | 3.68 | Ninjurin 1 | NINJ1 |
| 1030463 | 0.004 | 2.49 | ↑ | 3.30 | 4.62 | Prokineticin 2 | PROK2 |
| 3890326 | 0.011 | 2.02 | ↑ | 3.43 | 4.44 | Superoxide dismutase 2, mitochon. | SOD2 |
| MINIMALLY ANNOTATED | | | | | | | FROM NCBI |
| 6420563 | 0.023 | 2.00 | ↓ | 3.85 | 2.85 | LOC100129902 | RPS29P11 |
| 650735 | 0.01 | 2.09 | ↓ | 1.86 | 0.79 | LOC100131205 | RPL21P28 |
| 6650603 | 0.000 | 2.66 | ↓ | 1.95 | 0.54 | LOC100131905 | RPS27P21 |
| 7150414 | 0.003 | 2.31 | ↓ | 2.26 | 1.06 | LOC100132291 | RPS27P29 |
| 4670634 | 0.003 | 2.81 | ↑ | 1.69 | 3.18 | LOC100132394 | retired |
| 6580017 | 0.009 | 2.18 | ↓ | 2.81 | 1.69 | LOC100132742 | RPL17L |
| 2630347 | 0.001 | 2.04 | ↑ | 1.17 | 2.21 | LOC100134364 | retired |
| 3390674 | 0.002 | 2.01 | ↓ | 2.11 | 1.10 | LOC391370 | RPS12P4 |

TABLE 2-continued

Differentially expressed genes (DEG) sorted by functional grouping

| Probe ID | p Val | Fold Change | | Expression Level | | DEFINITION | SYMBOL |
|---|---|---|---|---|---|---|---|
| | | | | ABDOM | APPDX | | |
| 1170551 | 0.001 | 2.19 | ↓ | 1.55 | 0.42 | LOC646785 | RPS10P13 |
| 6960373 | 0.013 | 2.00 | ↓ | 2.23 | 1.23 | LOC644191 | RPS26P8 |
| 4540241 | 0.005 | 2.15 | ↑ | 1.10 | 2.21 | C5orf32 | CYSTM1 |

TABLE 3

A sixteen transcript set predictive of appendicitis

| PROBE_ID | SYMBOL | ProbeID | p | FC (abs) | Change | ABDOM expression level | APP expression level |
|---|---|---|---|---|---|---|---|
| ILMN_1701603 | ALPL | 6100356 | 0.001874699 | 2.84 | up | 3.63 | 5.14 |
| ILMN_1761566 | C5orf32 | 4540241 | 0.004890986 | 2.15 | up | 1.10 | 2.21 |
| ILMN_1697499 | HLA-DRB5 | 6370315 | 0.017076675 | 3.16 | up | −0.11 | 1.55 |
| ILMN_1680397 | IL8RB | 2900327 | 0.002848122 | 2.59 | up | 2.8 | 4.17 |
| ILMN_1661631 | LILRA3 | 6110037 | 0.007226919 | 2.36 | up | 2.38 | 3.62 |
| ILMN_3243593 | LOC100008588 | 3180609 | 0.001715004 | 2.69 | up | 1.04 | 2.47 |
| ILMN_1733559 | LOC100008589 | 6280504 | 0.005007231 | 2.05 | up | 1.2 | 2.23 |
| ILMN_3249578 | LOC100132394 | 4670634 | 0.003334389 | 2.81 | up | 1.69 | 3.18 |
| ILMN_3246805 | LOC100134364 | 2630347 | 8.80E−04 | 2.04 | up | 1.17 | 2.21 |
| ILMN_3293367 | LOC391370 | 3390674 | 0.001937386 | 2.01 | down | 2.11 | 1.1 |
| ILMN_3209193 | LOC644191 | 6960373 | 0.012769181 | 2.00 | down | 2.23 | 1.23 |
| ILMN_2155719 | NBPF10 | 1510681 | 0.012251468 | 2.01 | down | 3.56 | 2.55 |
| ILMN_1815086 | NINJ1 | 7380706 | 7.91E−04 | 2.10 | up | 2.61 | 3.68 |
| ILMN_1775257 | PROK2 | 1030463 | 0.004478186 | 2.49 | up | 3.3 | 4.62 |
| ILMN_1755115 | RPL23 | 380575 | 9.09E−05 | 2.14 | down | 1.49 | 0.39 |
| ILMN_2336781 | SOD2 | 3890326 | 0.010532255 | 2.02 | up | 3.43 | 4.44 |

Certain aspects of this expression pattern increase the confidence that some of these changes are non-random: 1) multiple probe sets identifying the same transcript (DEFA1), 2) 'hits' on highly related transcripts such as DEFA1 and DEFA3, as well as CXCR1 (aka IL8 receptor α) and IL8 receptor β.

TABLE 4

DEG gene symbols and Genbank IDs

| Probe ID | Gene Symbol | Definition | Genbank ID(s) |
|---|---|---|---|
| 6100356 | ALPL | *Homo sapiens* alkaline phosphatase, liver/bone/kidney (ALPL), transcript variant 1, mRNA. | AL592309 AB011406 BC066116 AB012643 BC136325 NM_000478 NM_001127501 AL359815 X53750 BC021289 AB209814 D87880 D87882 D87881 AK298085 M24429 BC126165 M24428 BC110909 D87877 D87887 D87876 CH471134 D87888 D87879 D87889 D87878 D87883 |

TABLE 4-continued

DEG gene symbols and Genbank IDs

| Probe ID | Gene Symbol | Definition | Genbank ID(s) |
|---|---|---|---|
| | | | AK312667 |
| | | | D87884 |
| | | | DA625627 |
| | | | D87875 |
| | | | D87885 |
| | | | D87874 |
| | | | D87886 |
| | | | DA631560 |
| | | | M24435 |
| | | | M24434 |
| | | | M24433 |
| | | | M24432 |
| | | | BC090861 |
| | | | M24431 |
| | | | M24430 |
| | | | AK293184 |
| | | | M24439 |
| | | | M24438 |
| | | | M24437 |
| | | | M24436 |
| | | | AK295608 |
| | | | X14174 |
| | | | AK097413 |
| 4540241 | C5orf32 | Homo sapiens chromosome 5 open reading frame 32 (C5orf32), mRNA. | BC023982 AJ245877 |
| | | | CH471062 |
| | | | BM919999 |
| | | | AC011379 |
| | | | CR607630 |
| | | | AK225992 |
| | | | BC013643 |
| | | | AK312045 |
| | | | CA310907 |
| | | | CR615127 |
| | | | CR603819 |
| | | | AC011380 |
| | | | NM_032412 |
| 6380672 | CA4 | Homo sapiens carbonic anhydrase IV (CA4), mRNA. | AK298710 AC025048 |
| | | | NM_000717 |
| | | | M83670 |
| | | | AK289715 |
| | | | BC069649 |
| | | | DA113846 |
| | | | L10953 |
| | | | L10954 |
| | | | L10955 |
| | | | L10951 |
| | | | AI990988 |
| | | | BC074768 |
| | | | CH471109 |
| | | | BC057792 |
| | | | CR541766 |
| 3440669 | CXCR1 | Homo sapiens chemokine (C-X-C motif) receptor 1 (CXCR1), mRNA. | CR542029 AY916763 |
| | | | AY916764 |
| | | | AY916762 |
| | | | CR541994 |
| | | | BC072397 |
| | | | DQ894895 |
| | | | L19591 |
| | | | L19592 |
| | | | AB032732 |
| | | | AY651785 |
| | | | M68932 |
| | | | U11871 |
| | | | AY916766 |
| | | | U11870 |
| | | | CR617846 |
| | | | AY916765 |
| | | | BC028221 |
| | | | X65858 |
| | | | AK312668 |
| | | | AB032730 |
| | | | AB032731 |
| | | | AY916769 |
| | | | CH471063 |
| | | | NM_000634 |
| | | | AY916772 |

TABLE 4-continued

DEG gene symbols and Genbank IDs

| Probe ID | Gene Symbol | Definition | Genbank ID(s) |
|---|---|---|---|
| 4540239 | DEFA1 | *Homo sapiens* defensin, alpha 1 (DEFA1), mRNA. | AY916773<br>AC097483<br>AK298647<br>AB032729<br>AB032728<br>AK309632<br>CA425329<br>DQ891718<br>AX405718 L12690<br>NM_004084<br>AF238378<br>AF200455<br>BC069423<br>X52053<br>AF233439<br>M26602<br>BC093791<br>DQ896798<br>DQ890546<br>DQ890545<br>NM_001042500<br>BC112188<br>M21130 |
| 870477 | DEFA1B | *Homo sapiens* defensin, alpha 1B (DEFA1B), mRNA. | AX405718 L12690<br>NM_004084<br>AF238378<br>AF200455<br>BC069423<br>X52053<br>AF233439<br>M26602<br>BC093791<br>DQ896798<br>DQ890546<br>DQ890545<br>NM_001042500<br>BC112188<br>M21130 |
| 4860128 | DEFA1B | *Homo sapiens* defensin, alpha 1B (DEFA1B), mRNA. | AX405718 L12690<br>NM_004084<br>AF238378<br>AF200455<br>BC069423<br>X52053<br>AF233439<br>M26602<br>BC093791<br>DQ896798<br>DQ890546<br>DQ890545<br>NM_001042500<br>BC112188<br>M21130 |
| 7150170 | DEFA1B | *Homo sapiens* defensin, alpha 1B (DEFA1B), mRNA. | AX405718 L12690<br>NM_004084<br>AF238378<br>AF200455<br>BC069423<br>X52053<br>AF233439<br>M26602<br>BC093791<br>DQ896798<br>DQ890546<br>DQ890545<br>NM_001042500<br>BC112188<br>M21130 |
| 2970747 | DEFA3 | *Homo sapiens* defensin, alpha 3, neutrophil-specific (DEFA3), mRNA. | L12691 EU176174<br>M23281<br>X13621<br>NM_005217<br>AF238378<br>BC027917<br>AF200455 |

TABLE 4-continued

DEG gene symbols and Genbank IDs

| Probe ID | Gene Symbol | Definition | Genbank ID(s) |
|---|---|---|---|
| 1450139 | FCGR3B | *Homo sapiens* Fc fragment of IgG, low affinity IIIb, receptor (CD16b) (FCGR3B), mRNA. | M21131<br>BC119706<br>AK316565 M24854<br>AL451067<br>BC128562<br>NM_000570<br>X07934<br>AB032414<br>Z46223<br>AK313219<br>X16863<br>DA672763<br>AJ581669 J04162 |
| 6370315 | HLA-DRB5 | *Homo sapiens* major histocompatibility complex, class II, DR beta 5 (HLA-DRB5), mRNA. | AB025256<br>AF112878 Y17695<br>AF112877<br>X65585<br>AF243537<br>AY050211<br>AF029286<br>U68391<br>AF029285<br>AY465115<br>AF029282<br>AY050208<br>AF029283<br>AY050207<br>M98436<br>M16955<br>AF327742<br>M16954<br>AF029281<br>M16956<br>AY663412<br>DQ835614<br>AY770514<br>M63216<br>AF011786<br>AY267905<br>AF029267<br>AJ251984<br>M77671<br>AY396024<br>AY267906<br>AF029273<br>AF029274<br>AF029275<br>DQ837166<br>AJ783982<br>AY050214<br>AF029270<br>AB112913<br>AF029271<br>AB112912<br>AF029272<br>AY770520<br>AJ242985<br>AY663404<br>U79027<br>U79025<br>U79026<br>AF288212<br>X99841<br>U59685<br>AL713966<br>M91001<br>D13412<br>AY641577<br>X64544<br>AJ566209<br>AF335232<br>U34602<br>X64548<br>Y13727<br>X64549<br>AF029291 |

TABLE 4-continued

DEG gene symbols and Genbank IDs

| Probe ID | Gene Symbol | Definition | Genbank ID(s) |
|---|---|---|---|
| | | | AJ252281 |
| | | | AY141137 |
| | | | EF078986 |
| | | | AY052549 |
| | | | AY884215 |
| | | | AJ506752 |
| | | | AM231063 |
| | | | AJ534885 |
| | | | AJ512947 |
| | | | M74032 |
| | | | M16086 |
| | | | X87210 |
| | | | M63197 |
| | | | M20429 |
| | | | AJ427352 |
| | | | AY247411 |
| | | | AY502108 |
| | | | M15839 |
| | | | Y17819 |
| | | | AF335230 |
| | | | L26306 |
| | | | X99895 |
| | | | U25638 |
| | | | AF047350 |
| | | | M57600 |
| | | | AY172512 |
| | | | DQ987876 |
| | | | AY179368 |
| | | | AY179367 |
| | | | AY179366 |
| | | | AJ491301 |
| | | | AJ867236 |
| | | | U95818 |
| | | | U41634 |
| | | | M14661 |
| | | | AJ506201 |
| | | | AF034858 |
| | | | EF419344 |
| | | | D14352 |
| | | | AF406781 |
| | | | D88310 |
| | | | U72264 |
| | | | AJ878425 |
| | | | AJ249726 |
| | | | DQ514604 |
| | | | DQ525634 |
| | | | AJ854064 |
| | | | U66721 |
| | | | AY899913 |
| | | | AJ245714 |
| | | | AJ245715 |
| | | | AJ245717 |
| | | | AM000036 |
| | | | X95656 |
| | | | U66826 |
| | | | AJ243897 |
| | | | AY277387 |
| | | | AJ243898 |
| | | | AJ580838 |
| | | | M27689 |
| | | | AJ311892 |
| | | | AF247534 |
| | | | AF247533 |
| | | | U37583 |
| | | | AY259126 |
| | | | AY277393 |
| | | | AY277390 |
| | | | AY277391 |
| | | | AK314834 |
| | | | AY259128 |
| | | | U72064 |
| | | | Z83201 |
| | | | X97291 |
| | | | DQ179043 |
| | | | AY054375 |
| | | | DQ179042 |

TABLE 4-continued

DEG gene symbols and Genbank IDs

| Probe ID | Gene Symbol | Definition | Genbank ID(s) |
|---|---|---|---|
| | | | U41489 |
| | | | AY504812 |
| | | | M81174 |
| | | | AY504813 |
| | | | AF329281 |
| | | | AJ297705 |
| | | | AF306862 |
| | | | AJ238410 |
| | | | AJ539471 |
| | | | M81171 |
| | | | Y09342 |
| | | | AY307897 |
| | | | D89917 |
| | | | U08275 |
| | | | U08274 |
| | | | M30182 |
| | | | M30181 |
| | | | AY663397 |
| | | | U95115 |
| | | | AB010270 |
| | | | AM159646 |
| | | | AF164346 |
| | | | DQ535034 |
| | | | AB010269 |
| | | | AY257483 |
| | | | AY429728 |
| | | | AJ515905 |
| | | | AY429723 |
| | | | M81180 |
| | | | AY877348 |
| | | | X73027 |
| | | | M57648 |
| | | | AF093411 |
| | | | DQ135944 |
| | | | AJ507780 |
| | | | AF089719 |
| | | | AJ297582 |
| | | | D49468 |
| | | | AY174184 |
| | | | AY174181 |
| | | | AB049832 |
| | | | AY050186 |
| | | | AF339884 |
| | | | AB062112 |
| | | | DQ140279 |
| | | | AJ404618 |
| | | | M20503 |
| | | | AJ854250 |
| | | | AF16923 9 |
| | | | NM_002125 |
| | | | U96926 |
| | | | M17377 |
| | | | AF052574 |
| | | | DQ179034 |
| | | | AF267639 |
| | | | M17379 |
| | | | AF142465 |
| | | | M17384 |
| | | | AJ507382 |
| | | | M59798 |
| | | | M17387 |
| | | | AF142466 |
| | | | AF029301 |
| | | | M17383 |
| | | | M17382 |
| | | | M32578 |
| | | | AY296120 |
| | | | AY296121 |
| | | | AY170862 |
| | | | AJ271159 |
| | | | EF495154 |
| | | | U26558 |
| | | | Y07590 |
| | | | AF142451 |
| | | | AJ871009 |
| | | | S79786 |

TABLE 4-continued

DEG gene symbols and Genbank IDs

| Probe ID | Gene Symbol | Definition | Genbank ID(s) |
|---|---|---|---|
| | | | AJ441130 |
| | | | AB106129 |
| | | | AF122887 |
| | | | AF201762 |
| | | | X96396 |
| | | | U17381 |
| | | | AJ289124 |
| | | | AJ306404 |
| | | | AY545466 |
| | | | DQ643390 |
| | | | DQ060439 |
| | | | D29836 |
| | | | AJ507425 |
| | | | AF186408 |
| | | | AF442519 |
| | | | AB087875 |
| | | | AB176444 |
| | | | AF186407 |
| | | | Z99006 |
| | | | U25442 |
| | | | AY048687 |
| | | | M15992 |
| | | | CH878642 |
| | | | AF142447 |
| | | | AY305859 |
| | | | AF142442 |
| | | | AY664400 |
| | | | AF142445 |
| | | | AY664401 |
| | | | AF450093 |
| | | | AF234175 |
| | | | X86803 |
| | | | AF490771 |
| | | | U31770 |
| | | | AF004817 |
| | | | AJ401148 |
| | | | BC009234 |
| | | | AF234181 |
| | | | AJ488066 |
| | | | AJ243327 |
| | | | FN430425 |
| | | | AF144080 |
| | | | AM084908 |
| | | | AY379480 |
| | | | M35159 |
| | | | L21755 |
| | | | AY331806 |
| | | | AF081676 |
| | | | AY457037 |
| | | | AK292140 |
| | | | AY765349 |
| | | | L41992 |
| 2900327 | IL8RB | Homo sapiens interleukin 8 receptor, beta (IL8RB), mRNA. | U11869 DA670033 |
| | | | U11866 |
| | | | AK290906 |
| | | | DQ895671 |
| | | | NM_001168298 |
| | | | DA674925 |
| | | | L19593 |
| | | | AB032733 |
| | | | AC124768 |
| | | | AB032734 |
| | | | U11873 |
| | | | U11872 |
| | | | DQ893661 |
| | | | AK312664 |
| | | | M73969 |
| | | | U11874 |
| | | | U11875 |
| | | | AY714242 |
| | | | AJ710879 |
| | | | U11876 |
| | | | U11877 |
| | | | CH471063 |
| | | | U11878 |
| | | | M94582 |

TABLE 4-continued

DEG gene symbols and Genbank IDs

| Probe ID | Gene Symbol | Definition | Genbank ID(s) |
|---|---|---|---|
| 6110037 | LILRA3 | Homo sapiens leukocyte immunoglobulin-like receptor, subfamily A (without TM domain), member 3 (LILRA3), mRNA. | BC037961<br>M99412<br>NM_001557<br>AF482762 AF482763<br>U91926<br>U91927<br>AF482766<br>AF482767<br>BC028208<br>AF482764<br>AF482765<br>NM_006865<br>AF025527<br>DQ894258<br>AF014923<br>AF014924<br>AF353733<br>AC010518<br>DQ891075<br>CH471135<br>AF482769<br>AF482768 |
| 3180609 | LOC100008588 | Homo sapiens 18S ribosomal RNA (LOC100008588), non-coding RNA. | NT_167214.1 |
| 6280504 | LOC100008589 | Homo sapiens 28S ribosomal RNA (LOC100008589), non-coding RNA. | AK225361 NM_033331<br>EF611343<br>NM_003671<br>AF023158<br>AF064104<br>AL133477<br>NM_001077181<br>AF064105<br>AL353578<br>AY675321<br>AK126388<br>CR601692<br>BC156666<br>BC050013<br>DA943563<br>CH471174<br>U13369<br>NR_003287<br>AL592188 |
| 6280504 | LOC100008589 | Homo sapiens 28S ribosomal RNA (LOC100008589), non-coding RNA. | NT_167214.1 |
| 6420563 | LOC100129902 | PREDICTED: Homo sapiens similar to mCG7602 (LOC100129902), mRNA, | NC_000004.10 |
| 650735 | LOC100131205 | PREDICTED: Homo sapiens hypothetical protein LOC100131205, transcript variant 3 (LOC100131205), mRNA. | NR_026911 |
| 6650603 | LOC100131905 | PREDICTED: Homo sapiens misc_RNA (LOC100131905), miscRNA. | NC_000012.10 |
| 7150414 | LOC100132291 | PREDICTED: Homo sapiens similar to hCG2027326 (LOC100132291), mRNA. | NC_000019.8 |
| 4670634 | LOC100132394 | PREDICTED: Homo sapiens hypothetical protein LOC100132394 (LOC100132394), mRNA. | n/a |
| 6580017 | LOC100132742 | PREDICTED: Homo sapiens hypothetical protein LOC100132742, transcript variant 1 (LOC100132742), mRNA. | NC_000001.9 |
| 2630347 | LOC100134364 | PREDICTED: Homo sapiens hypothetical protein LOC100134364 (LOC100134364), mRNA. | n/a |

TABLE 4-continued

DEG gene symbols and Genbank IDs

| Probe ID | Gene Symbol | Definition | Genbank ID(s) |
|---|---|---|---|
| 3390674 | LOC391370 | PREDICTED: *Homo sapiens* similar to hCG1818387 (LOC391370), mRNA. | NC_000002.10 |
| 3190348 | LOC440927 | PREDICTED: *Homo sapiens* similar to 60S acidic ribosomal protein P1, transcript variant 4 (LOC440927), mRNA. | n/a |
| 6960373 | LOC644191 | PREDICTED: *Homo sapiens* similar to hCG15685, transcript variant 1 (LOC644191), mRNA. | NC_000017.9 |
| 6270307 | LOC644934 | PREDICTED: *Homo sapiens* similar to 40S ribosomal protein S26, transcript variant 1 (LOC644934), mRNA. | AL353735 AC225613 AC090543 AC034102 CH471054 DQ896038 CH471057 AL136526 BC105798 AC098847 AB007161 AC006463 U41448 AC008065 AB007160 X69654 AP004217 DQ895081 X79236 AL138767 AV681946 AC126544 CH236947 DQ891895 BC013215 BC070220 BC105276 DQ896089 AC012391 DQ892791 AC027373 NM_001029 AC004057 X77770 AC025518 BC015832 CR611958 BC002604 |
| 1170551 | LOC646785 | PREDICTED: *Homo sapiens* misc RNA (LOC646785), miscRNA. | NC_000006.10 |
| 6960195 | LOC650646 | PREDICTED: *Homo sapiens* similar to 40S ribosomal protein S26 (LOC650646), mRNA. | AL445193 CH471059 |
| 1510681 | NBPF10 | *Homo sapiens* neuroblastoma breakpoint family, member 10 (NBPF10), mRNA. XM_930727 XM_930739 XM_930751 XM_930759 XM_930766 XM_930776 XM_930785 XM_930797 XM_930808 XM_930830 XM_930841 XM_930850 XM_930862 XM_930872 XM_930880 XM_930889 XM_930897 XM_930903 XM_930910 XM_930917 XM_930926 XM_930936 XM_930943 XM_930951 XM_930954 XM_930961 XM_930967 XM_930975 XM_930985 XM_930993 XM_931003 XM_931009 | NM_001101663 BC094705 AK055895 AL049742 AF379606 AK095030 AF379607 BC034418 CR599564 XM_002346226 CR608846 BC169317 BC169318 BC169316 BC094841 DB300232 AF380582 NM_001037675 BC086308 AL117237 |

TABLE 4-continued

DEG gene symbols and Genbank IDs

| Probe ID | Gene Symbol | Definition | Genbank ID(s) |
|---|---|---|---|
| | | XM_931015 XM_931021 | AF380580 |
| | | XM_931027 XM_931033 | NM_183372 |
| | | XM_931038 XM_931044 | BC063799 |
| | | XM_931049 XM_931055 | BX546486 |
| | | XM_931060 XM_931066 | BC027348 |
| | | XM_931069 XM_931072 | AL592284 |
| | | XM_931076 XM_931080 | NM_001039703 |
| | | XM_931084 XM_931090 | AC026900 |
| | | XM_931096 XM_931102 | AK302413 |
| | | XM_931110 XM_931119 | AF379624 |
| | | XM_931125 XM_931131 | NM_015383 |
| | | XM_931137 XM_931138 | AF379626 |
| | | XM_931145 XM_931149 | AF379627 |
| | | XM_931157 XM_931161 | AF379628 |
| | | XM_931164 XM_931169 | AK294944 |
| | | XM_931174 XM_931178 | XM_001726946 |
| | | XM_931183 XM_931188 | AK092351 |
| | | XM_931191 XM_931196 | AF379620 |
| | | XM_931202 XM_931208 | AF379621 |
| | | XM_931213 XM_931221 | AF379622 |
| | | XM_931229 XM_931234 | AF379623 |
| | | XM_931240 XM_931245 | AK054850 |
| | | XM_931251 XM_931255 | AL359176 |
| | | XM_931259 XM_931264 | XM_001717398 |
| | | XM_931269 XM_931277 | AF379615 |
| | | XM_931282 XM_931291 | AF379616 |
| | | XM_931299 XM_931308 | AF379613 |
| | | XM_931317 XM_931322 | AF131738 |
| | | XM_931328 XM_931335 | AF379614 |
| | | | AL355149 |
| | | | AF379619 |
| | | | AL138796 |
| | | | BX511041 |
| | | | AK290302 |
| | | | AF379617 |
| | | | AL050141 |
| | | | AF379618 |
| | | | BC021111 |
| | | | AF379611 |
| | | | AF379612 |
| | | | AY894574 |
| | | | BC010124 |
| | | | AY894573 |
| | | | BC148331 |
| | | | AY894572 |
| | | | AL040349 |
| | | | AY894571 |
| | | | AY894570 |
| | | | BC071995 |
| | | | AY894579 |
| | | | AY894578 |
| | | | AY894577 |
| | | | AL592307 |
| | | | AY894576 |
| | | | AY894575 |
| | | | AL137798 |
| | | | AK290142 |
| | | | AI865471 |
| | | | AF419617 |
| | | | XM_001715810 |
| | | | AF419616 |
| | | | AF419619 |
| | | | AF419618 |
| | | | AK095459 |
| | | | AF379632 |
| | | | AY894583 |
| | | | AF379631 |
| | | | AL356004 |
| | | | AY894582 |
| | | | AF379634 |
| | | | AY894585 |
| | | | BC110431 |
| | | | AF379630 |
| | | | AY894581 |
| | | | AK125792 |
| | | | AY894580 |

TABLE 4-continued

DEG gene symbols and Genbank IDs

| Probe ID | Gene Symbol | Definition | Genbank ID(s) |
|---|---|---|---|
| | | | AL139152 |
| | | | BC167783 |
| | | | AK294414 |
| | | | AF379635 |
| | | | NM_017940 |
| | | | AF420437 |
| | | | BQ890458 |
| | | | AK000726 |
| | | | BC136292 |
| | | | CR600619 |
| | | | AL954711 |
| | | | BC071723 |
| | | | AF161426 |
| | | | BI552657 |
| | | | AB051480 |
| | | | CR610345 |
| | | | AK097180 |
| | | | BC023087 |
| | | | BX648497 |
| | | | AL022240 |
| | | | AL832622 |
| | | | AB033071 |
| | | | AY894561 |
| | | | BC013805 |
| | | | AY894563 |
| | | | AY894562 |
| | | | BC066930 |
| | | | AY894565 |
| | | | AY894567 |
| | | | AY894566 |
| | | | BX538005 |
| | | | AY894569 |
| | | | AY894568 |
| | | | BX842679 |
| | | | NM_173638 |
| | | | DQ786323 |
| | | | AK299360 |
| | | | NM_001170755 |
| | | | BC093404 |
| | | | AK123260 |
| 7380706 | NINJ1 | Homo sapiens ninjurin 1 (NINJ1), mRNA. | AL451065 BC048212 |
| | | | AK094530 |
| | | | BT007164 |
| | | | U91512 |
| | | | BC019336 |
| | | | AF029251 |
| | | | CH471089 |
| | | | U72661 |
| | | | BC004440 |
| | | | CR608271 |
| | | | CR595190 |
| | | | NM_004148 |
| | | | BC000298 |
| 1030463 | PROK2 | Homo sapiens prokineticin 2 (PROK2), mRNA. | AC096970 AY349131 |
| | | | CS023558 |
| | | | BC098110 |
| | | | CH471055 |
| | | | NM_021935 |
| | | | BC069395 |
| | | | AF333025 |
| | | | NM_001126128 |
| | | | BC098162 |
| | | | BC096695 |
| | | | AF182069 |
| 380575 | RPL23 | Homo sapiens ribosomal protein L23 (RPL23), mRNA. | X52839 AC110749 |
| | | | BC034378 |
| | | | BC106061 |
| | | | CR604268 |
| | | | X55954 |
| | | | CR610098 |
| | | | BC104651 |
| | | | CH471152 |
| | | | NM_000978 |
| | | | AB061827 |
| | | | AL136089 |
| | | | BC003518 |

TABLE 4-continued

DEG gene symbols and Genbank IDs

| Probe ID | Gene Symbol | Definition | Genbank ID(s) |
|---|---|---|---|
| 990273 | RPL37A | Homo sapiens ribosomal protein L37a (RPL37A), mRNA. | DQ893218<br>CA437923<br>BC062716<br>DQ896547<br>BC010114<br>AK024749<br>CR618026 CR542152<br>BC016748<br>L22154<br>CH471063<br>BC047872<br>CR613913<br>BC039030<br>BC014262<br>BC067789<br>NM_000998<br>L06499<br>CD249666<br>AC073321<br>BC063476<br>X66699<br>BC082239<br>AK291857<br>BC000555<br>AK289472<br>D28355 |
| 5890730 | RPS26L | PREDICTED: Homo sapiens 40S ribosomal protein S26-like (RPS26L), misc RNA. | AL136526 |
| 6560376 | RPS26P11 | Homo sapiens ribosomal protein S26 pseudogene 11 (RPS26P11), non-coding RNA. | NR_002309 AL929401<br>AW972305 |
| 650349 | RPS28 | Homo sapiens ribosomal protein S28 (RPS28), mRNA. | AB007164 CH471076<br>AU126783<br>BC021239<br>AC107983<br>L05091<br>AC005011<br>CR606185<br>DQ891357<br>U58682<br>CR603137<br>AK293636<br>BC070217<br>BC070218<br>CH471139<br>AC010323<br>AK301638<br>BC018810<br>DQ894538<br>CR457055<br>CH236952<br>NM_001031<br>AB061846<br>BC000354<br>AK311925 |
| 3890326 | SOD2 | Homo sapiens superoxide dismutase 2, mitochondrial (SOD2), nuclear gene encoding mitochondrial protein, transcript variant 2, mRNA. | X65965 BC035422<br>CH471051<br>BU164685<br>DQ003134<br>DQ890587<br>Y00472<br>X59445<br>AK097395<br>AM392836<br>AY280721<br>AK304766<br>AY280720<br>AY267901<br>BT006967<br>BU741675<br>AY280719<br>AY280718<br>Y00985 |

TABLE 4-continued

DEG gene symbols and Genbank IDs

| Probe ID | Gene Symbol | Definition | Genbank ID(s) |
|---|---|---|---|
| | | | NM_001024465 |
| | | | NM_001024466 |
| | | | BC016934 |
| | | | CR626136 |
| | | | AK296809 |
| | | | S77127 |
| | | | L34157 |
| | | | X14322 |
| | | | BC001980 |
| | | | NM_000636 |
| | | | D83493 |
| | | | M36693 |
| | | | AL691784 |
| | | | X07834 |
| | | | AK313082 |
| | | | X15132 |
| | | | AL050388 |
| | | | AL135914 |
| | | | DQ893752 |
| | | | BC012423 |
| | | | BG699596 |
| | | | BM994509 |

TABLE 5A

PLSD loading weights for genes from Table 2:

| PROBE_ID | SYMBOL | PLSD Loading weight for Abdominal discomfort | PLSD Loading weight for Appendicitis |
|---|---|---|---|
| ILMN_1701603 | ALPL | 0.29783 | −0.29783 |
| ILMN_1761566 | C5orf32 | −0.25526 | 0.25526 |
| ILMN_1695157 | CA4 | −0.01612 | 0.01612 |
| ILMN_1662524 | CXCR1 | −0.06819 | 0.06819 |
| ILMN_2193213 | DEFA1 | −0.06522 | 0.06522 |
| ILMN_1679357 | DEFA1B | 0.04740 | −0.04740 |
| ILMN_1725661 | DEFA1B | −0.01104 | 0.01104 |
| ILMN_2102721 | DEFA1B | 0.03026 | −0.03026 |
| ILMN_2165289 | DEFA3 | −0.04788 | 0.04788 |
| ILMN_1728639 | FCGR3B | 0.04584 | −0.04584 |
| ILMN_1697499 | HLA-DRB5 | −0.33313 | 0.33313 |
| ILMN_1680397 | IL8RB | −0.16264 | 0.16264 |
| ILMN_1661631 | LILRA3 | −1.50443 | 1.50443 |
| ILMN_3243593 | LOC100008588 | 0.33584 | −0.33584 |
| ILMN_1733559 | LOC100008589 | −0.27838 | 0.27838 |
| ILMN_3256742 | LOC100129902 | 0.17543 | −0.17543 |
| ILMN_3214532 | LOC100131205 | 0.57084 | −0.57084 |
| ILMN_3275489 | LOC100131905 | 0.42307 | −0.42307 |
| ILMN_3275345 | LOC100132291 | 0.01674 | −0.01674 |
| ILMN_3249578 | LOC100132394 | −0.38482 | 0.38482 |
| ILMN_3202734 | LOC100132742 | 0.14064 | −0.14064 |
| ILMN_3246805 | LOC100134364 | −0.24811 | 0.24811 |
| ILMN_3293367 | LOC391370 | 0.21413 | −0.21413 |
| ILMN_1689712 | LOC440927 | 0.10489 | −0.10489 |
| ILMN_3209193 | LOC644191 | −0.25270 | 0.25270 |
| ILMN_1678522 | LOC644934 | −0.09154 | 0.09154 |
| ILMN_3210538 | LOC646785 | 0.01680 | −0.01680 |
| ILMN_1726647 | LOC650646 | −0.10099 | 0.10099 |
| ILMN_2155719 | NBPF10 | 0.51417 | −0.51417 |
| ILMN_1815086 | NINJ1 | −0.62920 | 0.62920 |
| ILMN_1775257 | PROK2 | 0.31264 | −0.31265 |
| ILMN_1755115 | RPL23 | 0.42432 | −0.42433 |
| ILMN_2051519 | RPL37A | 0.04629 | −0.04629 |
| ILMN_1750636 | RPS26L | 0.17768 | −0.17768 |
| ILMN_2180866 | RPS26P11 | −0.00077 | 0.00077 |
| ILMN_1651228 | RPS28 | 0.03448 | −0.03448 |
| ILMN_2336781 | SOD2 | −0.28727 | 0.28727 |

TABLE 5B

PLSD loading weights for genes from Table 3:

| PROBE_ID | SYMBOL | PLSD Loading weight for Abdominal discomfort | PLSD Loading weight for Appendicitis |
|---|---|---|---|
| ILMN_1701603 | ALPL | 0.30 | −0.30 |
| ILMN_1761566 | C5orf32 | −0.26 | 0.26 |
| ILMN_1697499 | HLA-DRB5 | −0.33 | 0.33 |
| ILMN_1680397 | IL8RB | −0.16 | 0.16 |
| ILMN_1661631 | LILRA3 | −1.50 | 1.50 |
| ILMN_3243593 | LOC100008588 | 0.34 | −0.34 |
| ILMN_1733559 | LOC100008589 | −0.28 | 0.28 |
| ILMN_3249578 | LOC100132394 | −0.38 | 0.38 |
| ILMN_3246805 | LOC100134364 | −0.25 | 0.25 |
| ILMN_3293367 | LOC391370 | 0.21 | −0.21 |
| ILMN_3209193 | LOC644191 | −0.25 | 0.25 |
| ILMN_2155719 | NBPF10 | 0.51 | −0.51 |
| ILMN_1815086 | NINJ1 | −0.63 | 0.63 |
| ILMN_1775257 | PROK2 | 0.31 | −0.31 |
| ILMN_1755115 | RPL23 | 0.42 | −0.42 |
| ILMN_2336781 | SOD2 | −0.29 | 0.29 |

Functional Analysis of DEG Transcripts.

Of the well annotated transcripts, several had prior published relationships to infection, immunity, or inflammation, or stress/injury: notably, alkaline phosphatase liver/bone/kidney isoform (ALPL), carbonic anhydrase IV (CA4), chemokine (C-X-C motif) receptor 1 (CXCR1), defensin α1 (DEFA1), defensin 3 (DEFA3), IgG Fc receptor IIb (FCGR3B/CD16B), interleukin 8 receptor β (IL8RB), ninjurin 1, (NINJ1), prokinectin 2 (PROK2), and superoxide dismutase 2 (SOD2). In addition to their logical connection to appendicitis, which often has an infectious etiology, certain aspects of this expression pattern increase the confidence that some of these changes are non-random: 1) multiple probe sets identifying the same transcript (DEFA1), 2) 'hits' on highly related transcripts, such as DEFA1 and DEFA3, as well as CXCR1 (aka IL8 receptor β) and IL8 receptor β.

Defensins. To understand the defensin pathway, the 5 α-defensin transcripts in the DEG list, which are all variant transcripts from the DEFA locus at 8p21.3, were averaged to create a 'defensin score', and then compared between groups (Table 1). Using a threshold determined by the mean of all 20 patients (1.87), 6 of 9 (67%) patients with other abdominal disorders showed elevated defensins, while only 1 of 11 (9%) of appendicitis patients had elevated defensin mRNA (see defensin cluster in FIG. 2). Surprisingly, the defensin score was essentially uncorrelated with white blood cell count (WBC) (r=0.07) and neutrophil % (r=0.15).

Other immune/inflammatory pathways. Interestingly, 3 of the 37 DEG (LILRA3, CXCR1/IL8RA, FCGR3A), which were higher in appendicitis patients compared to abdominal pain patients, are near or exact matches to transcripts discovered previously as down-regulated by exposure of isolated human neutrophils to E. Coli [18]. However, across the 20 patients, they were not inversely correlated with defensin expression (LILRA=0.02, CXCR1=−0.02, FCGR3A=−0.33), suggesting they are regulated independently of infectious markers. Other transcripts were readily associated with tissue injury or inflammation, but not previously associated with pathogen infection. For instance, NINJ1 was identified as a transcript strongly upregulated after peripheral nerve injury [19]. PROK2 is elevated in colitis tissue [20], which, like appendicitis, is an inflammatory condition in the GI tract. Likewise, ALPL has a well-known role in modulating diverse inflammatory conditions not limited to infectious disease [21].

Ribosomal transcripts. While it is widely assumed that ribosomal RNAs (rRNA), such as 18S and 28S non-coding RNAs are 'invariant', or 'housekeeping' transcripts, there is considerable evidence that they are carefully regulated in cases such as granulocyte activation [22], and differ significantly in prostate cancer [23], and in hepatitis C infected livers [24]. In fact, early studies with PHA-activated human lymphocytes demonstrated as much as 8-fold increases in rRNA levels within 20 hours [25,26]. Furthermore, if the observed changes were due to some type of loading or processing anomaly, then we would expect all of the ribosomal RNAs to be affected in the same direction, when in fact, 18S and 28S noncoding transcripts were increased in appendicitis, but most of the transcripts coding for ribosomal proteins were decreased, suggesting that this is a regulated process.

Minimally annotated transcripts. Of the 37 DEG, 11 transcripts were minimally annotated, i.e. 'predicted transcript', but further manual annotation using NCBI Gene revealed high likelihood assignments. Remarkably, 8 of the 11 transcripts were identified as ribosomal protein pseudogenes, which is quite unlikely to have occurred by chance. Two transcripts have been discontinued, and the eleventh was identified as CYSTM1 (C5ORF32), which is a cysteine-rich transmembrane module-containing protein that 2-hybrid screens identified as an inhibitor of the glucagon-like peptide 1 receptor (GILP-IR) [27].

Prediction of Appendicitis from DEG.

Figure 3:
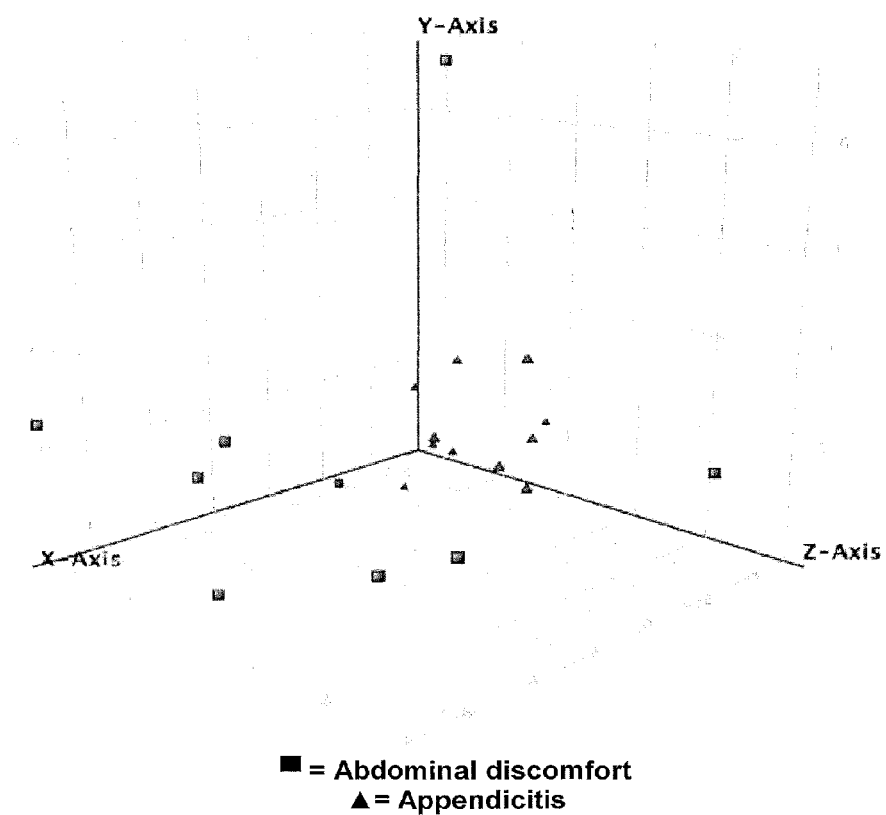
FIG. 3 shows a graph displaying the Partial Least Squares Discriminant (PLSD) Model for classification of appendicitis from RNA biomarkers.
Figure 4:
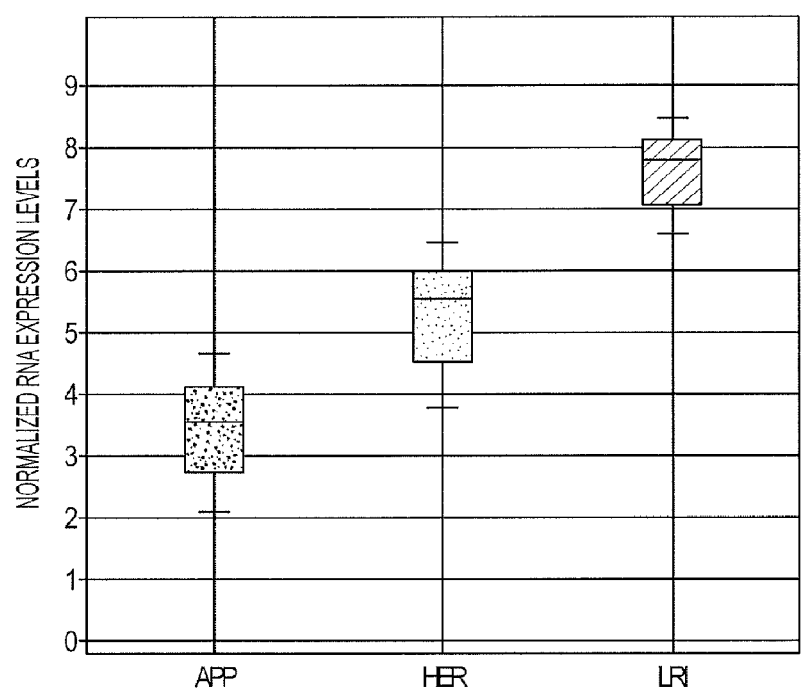
FIG. 4 is a graph showing results of defensins in appendicitis, hernia, and lower respiratory infection patients.

The PLSD model built on the 37 DEG list, was 100% accurate and specific within the discovery set, which is not surprising given the ability of PLSD models to accurately 'fit' data to outcomes. As shown in FIG. 3, the first 3 latent factors in the PLSD model demonstrate tight clustering of the appendicitis patients (▲) distinct from patients presenting with other abdominal pain (■). Clearly, 7 of 9 abdominal patients can be discriminated by only the first latent factor (t0, X-axis). Two abdominal patients, one with a GI bleed and one with diverticulitis, are poorly discriminated by the t0 latent factor shown in the X-axis, but are readily discriminated by one of the two other factors (Y or Z axis). To determine whether all 37 transcripts were necessary for prediction, 16 transcripts with a loading of >0.2 in the PLSD model were used to rebuild a new PLSD prediction model (Table 3, above). This smaller model, which omitted the defensins, remained quite strong, predicting 100% of abdominal cases, 90.9% of appendicitis cases, for an overall accuracy of 95%.

Based on these data, a highly predictive model can be generated by observing expression level patterns utilizing as few as 3 RNA transcripts. Of course the more levels that are measured, the more sensitive and predictive the patterns become. Accordingly, the present invention can use the pattern generated from 3 or more RNA transcripts, 4 or more RNA transcripts, 5 or more RNA transcripts, 6 or more RNA transcripts, 7 or more RNA transcripts, 8 or more RNA transcripts, 9 or more RNA transcripts, 10 or more RNA transcripts, 12 or more RNA transcripts, 14 or more RNA transcripts, or 16 or more RNA transcripts. The only minimum is that the number and selection of transcripts define a pattern that distinguishes appendicitis from other causes of abdominal pain. In embodiments, the method is at least 75% accurate, for example at least 80% accurate, at least 90% accurate, or at least 95% accurate.

FIG. 3 shows a graph displaying the Partial Least Squares Discriminant (PLSD) Model for classification of appendicitis from RNA biomarkers. In FIG. 3, DEGs were analyzed by PLSD to compose a classification model for appendicitis based on RNA biomarkers in blood. The 3D plot shows the 20 patients in the discovery set as partitioned by the first 3 of 4 latent factors in the PLSD model. The ■ represent abdominal pain patients (n=9), and ▲ shows the cluster of appendicitis patients (n=11), as a function of the t0 latent factor (X-axis), the t1 factor (Y-axis), and the t2 factor (Z-axis). The majority of patients (7/9) are accurately classified by the t0 component alone.

Validation of PLSD Prediction Model in Unrelated Samples.

To determine the robustness of the prediction model, a separate group of patients derived from the same overall cohort were similarly processed for whole blood RNA, and hybridized independently to Illumina HT 12v4 Beadchip arrays. With only minimal normalization to correct for minor loading and hybridization differences, the PLSD prediction model was applied to the normalized values for the 37 transcripts in the model. The PLSD prediction model correctly identified 8 of 9 true appendicitis patients (88.9%) and predicted 3 of 4 patients (75%) with hernias as being 'abdominal pain'. Nearly 90% sensitivity in an unrelated cohort quantified on a different microarray run is encouraging toward the potential robustness of the model. Notably, the PLSD model includes no clinical variables, such as fever or white cell count.

Behavior of the RNA Biomarkers in Non-Appendicitis Infections.

Figure 5:
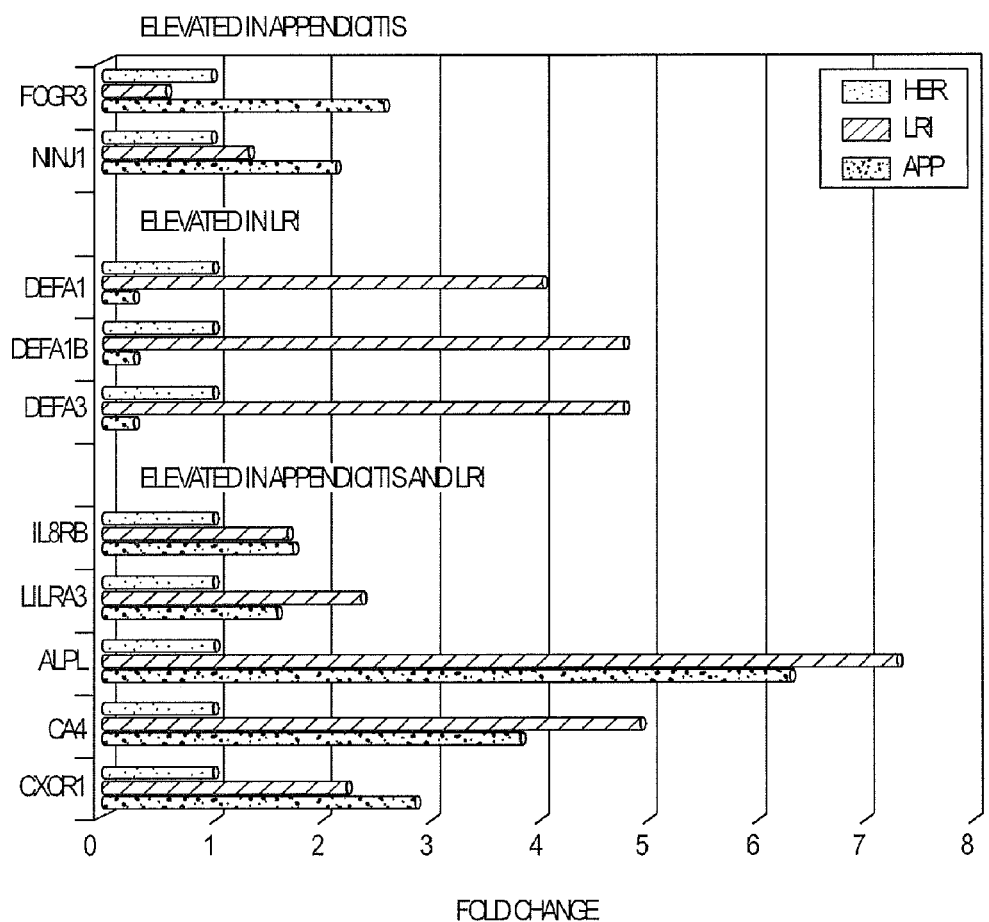
FIG. 5 shows the behavior of selected transcripts in a validation cohort.

In 5 patients clinically diagnosed with LRI, which were not included in PLSD training, the model predicts 4 of 5 as appendicitis (80%), suggesting that the model may be sensitive to generalized infectious or inflammatory signals in blood. Using the 16 DEG model, only 60% were diagnosed as appendicitis. As shown in FIG. 5, some transcripts, such as FCGR3 and NINJ1, were relatively selectively elevated in APP, but not LRI. Other transcripts, especially defensins, were much more sensitive to LRI than APP, showing 4-5 fold elevations in LRI versus HER, and 20-fold elevations in LRI vs APP. Most transcripts, as demonstrated by IL8Rβ, LILRA3, and ALPL, showed roughly similar changes in LRI and APP. Of the 37 transcripts, 10 are relatively selective for APP, 8 are selective for LRI, and 19 behave similarly in both APP and LRI.

FIG. 5 shows graphs displaying the behavior of DEG biomarkers in a validation cohort. In FIG. 5, the 37 DEG biomarker set was applied to transcript expression levels in unrelated patients presenting at the ER for either appendicitis (APP, green bars), lower respiratory infection (LRI, red bars), or hernias (HER, blue bars). Representative transcripts, such as Fc gamma receptor 3 (FCGR3) and ninjurin 1 (NINJ1) are shown, in which the transcript behaves with relatively selective induction in APP, relative to HER or LRI. Conversely, transcripts in the defensin family (DEFA1, DEFA3), are significantly elevated in HER patients, relative to APP, but are strikingly induced in LRI patients. Most transcripts, such as alkaline phosphatase (ALPL) and the IL8 receptors (IL8RB, CXCR1), were induced in both APP and LRI patients.

Discussion

Currently, there are no FDA-approved serum or urine biomarkers for abdominal pain or appendicitis. As noted earlier, abdominal pain is one of the most common complaints in the ED, and thus blood biomarkers represent an important unmet need in clinical medicine. In this discovery and validation study, we have identified a small set of RNA transcripts associated with appendicitis. Overall, a prediction model built on these markers was able to differentiate appendicitis from other forms of intra-abdominal pathology, such as diverticulitis and hernias. Appendicitis is thought to be an inflammatory disease, similar to diverticulitis or colitis; however, there was differing activation of certain mRNA biomarkers between these conditions. Furthermore, the 37 DEG markers do not correlate with white blood cell count, per se, but a careful examination of the transcripts suggests that the RNA biomarkers may be measuring the activation state of immune cells, especially neutrophils.

The pattern of transcriptome changes in blood may help to refine our understanding of the etiology and progression of acute appendicitis, as shown schematically in FIG. 9. The classic explanation for appendicitis is that a fecalith or lymphoid hyperplasia block the outflow of the appendix, resulting in obstruction and ischemia [28]. Outflow obstruction may produce local changes that favor undesirable changes in the appendix microbiome. Several recent studies, including next-generation sequencing (NGS) of the 16S regions of the microbiome, have suggested that relatively selective changes infusobacteria species are associated with appendicitis [29-32]. Fusobacteria, a type of gram-negative bacteria, can induce toxicity in adjacent host cells, and colitis-like symptoms in mice, potentially by producing butyric acid (butyrate) [33]. RT-PCR analysis confirms that inflamed appendix tissue has elevated α-defensin and IL-8 mRNA levels [34]. Likewise, *Fusobacterium nucleatum* biofilms stimulate IL-8 production in human oral epithelium cell lines [35] and *Fusobacterium necrophorum* induces IL-8 production in cultured mesothelial cells [36].

FIG. 6 shows a schematic of a model of appendicitis biomarker pathophysiology. It is believed that compacted fecal bodies, termed fecaliths, may occlude the outflow tract of the appendix, causing inflammatory conditions that are conducive to infection in the appendix. Microbiome analysis of inflamed appendices typically indicates a predominance of biofilm-forming bacteria, such as fusobacteria. The biofilm protects the bacteria from antibiotics, and from direct immune attack, but soluble factors produced by the bacteria, such as LPS (endotoxins) and butyrate, or IL-8, can diffuse into adjacent lymphatic and circulatory beds to activate neutrophils. The primed neutrophils respond with elevated transcript levels of alkaline phosphatase (ALPL), interleukin-8 receptor beta (IL8RB) and related biomarkers of local infection. Background images of appendix and neutrophil courtesy of Blausen.com staff, *Wikiversity Journal of Medicine*.

Thus, the absence of elevated α-defensin transcripts in the presence of elevated levels of mRNA for both IL-8 receptors suggests that circulating immune cells are primed by IL-8 produced in the inflamed appendix. However, it seems likely that the immune cells are not directly contacting the bacterial infection, which would elevate defensins, as demonstrated clearly in the LRI patients.

In addition to the IL-8 receptors, several other transcripts appear to be plausible biomarkers of localized inflammation. Notably, ALPL, along with IL8RB/CXCR2, was identified as an expression biomarker of asthma inflammatory subtypes [37]. In addition to these interesting innate immune markers, the results revealed unexpected changes in the ribosomal system. Humans utilize 4 ribosomal RNAs, which are non-coding (5S, 5.8S, 18S, 28S), and ~80 ribosomal proteins to build multimeric translation complexes. Additionally, there are ~2000 ribosomal protein pseudogenes, which are thought to derive from inactivated duplications, but may be processed to varying degrees, and could have regulatory functions [38]. Transcripts for 18S and 28S, both originating from multiple 45S genes, were increased in the appendicitis blood RNA, which could be due to both increased transcription from active rDNA genes [39], as well engagement of previously inactive rDNA transcription units [26]. Conversely, most of the coding transcripts, such as RPLP1 and RPS26, were decreased in the blood of appendicitis patients. Because the specific pattern of ribosomal proteins defines the type of RNAs that are engaged and translated [40], it is possible that the translational machinery is being re-geared to adapt to a new demand. Unexpectedly, most of the poorly annotated transcripts mapped to ribosomal protein pseudogenes, suggesting that either the probesets are incorrectly detecting a change in coding ribosomal protein transcripts, or the pseudogenes are somehow regulated in conjunction with the reconfigured translational machinery. Conceptually, the pattern of chemokine, defensin, stress-related, and ribosomal processing changes is consistent with the immune system being 'primed' as the immune cells pass through an inflammatory field created by a localized biofilm infection.

Other investigators have sought to develop protein biomarkers for appendicitis in the blood, such as bilirubin [41], C-reactive protein (CRP) [42], and pro-calcitonin (PCT) [43]. However, recent comparisons of these biomarkers had difficulty improving on a purely clinical prediction model, such as the Alvarado score (ROC=0.74, vs CRP=0.61, PCT=0.69) [44]. Recently, a combination of WBC, CRP, and MRP8/14 (S100A8/S100A9) was shown to be 96% sensitive, but 43% specific for acute appendicitis [42]. Likewise, a multivariate model built on plasma protein levels of serum amyloid (SAA), myeloperoxidase (MPO), and MMP9 was less diagnostic than a largely clinical model (ROC=0.71 vs 0.91 clinical model) [45].

While RNA-based diagnostic tests are currently on the market for breast cancer progression (MammaPrint, OncoType Dx), transplant rejection (AlloMap), and coronary artery disease (CorusCAD), this is the first report to assess blood RNA as a potential biomarker of appendicitis. Among the strengths of the present approach is that the test and validation sets included controls for surgical, inflammatory, and infectious factors. Further, the RNA profiling was broad and largely unbiased, and detected the same key pathways in the test and validation study.

Genome-wide RNA transcript profiling is thus demonstrated as being capable of identifying biomarkers of appendicitis. The detected biomarkers are consistent with prior published evidence that fusobacteria biofilms in the appendix may be an important putative mechanism in appendicitis.

By assaying the RNA levels by microarray analysis, alternative methods of assaying RNA levels can be applied in the steps of this invention. Examples of alternative methods including are real-time RT-PCR, real-time PCR, quantitative RT-PCR, qPCR, RT-PCR array, RNA sequencing (RNA-Seq), northern blot, and serial analysis of gene expression (SAGE), measuring protein expression.

Patterns of RNA levels define biomarkers that identify appendicitis. Differential expression of RNA levels of a gene often coincide with differential expression levels of the resultant proteins translated from the RNA. For this reason, measuring the protein expression level patterns that correlate to the identified differentially expressed genes is an alternative method of diagnosing appendicitis. Protein expression levels can be measured from serum samples by a number of means including western blot, enzyme-linked immunosorbent assay (ELISA), mass spectrometry, and other means that utilize antibody detection of proteins. Similar methods of testing as described for the RNA biomarkers can be used by replacing RNA measurement with protein measurement and determining suitable patterns. According to his embodiment, measuring the protein expression level patterns will diagnose appendicitis. In some embodiments, antibodies against specific proteins can be generated and used to measure protein expression levels.

REFERENCES FOR BACKGROUND AND EXAMPLE 1

1. Bhuiya F, Pitts S, McCaig L (2010) Emergency Department visits for chest pain and abdominal pain: United States, 1999-2008. CDC, NCHS Data Brief 43.
2. Charfi S, Sellami A, Affes A, Yaich K, Mzali R, et al. (2014) Histopathological findings in appendectomy specimens: a study of 24,697 cases. Int J Colorectal Dis 29: 1009-1012.
3. Drake F T, Florence M G, Johnson M G, Jurkovich G J, Kwon S, et al. (2012) Progress in the diagnosis of appendicitis: a report from Washington State's Surgical Care and Outcomes Assessment Program. Ann Surg 256: 586-594.
4. Seetahal S A, Bolorunduro O B, Sookdeo T C, Oyetunji T A, Greene W R, et al. (2011) Negative appendectomy: a 10-year review of a nationally representative sample. The American Journal of Surgery 201: 433-437.
5. Kirkil C, Karabulut K, Aygen E, Ilhan Y S, Yur M, et al. (2013) Appendicitis scores may be useful in reducing the costs of treatment for right lower quadrant pain. Ulus Travma Acil Cerrahi Derg 19: 13-19.
6. Memon Z A, Irfan S, Fatima K, Iqbal M S, Sami W (2013) Acute appendicitis: diagnostic accuracy of Alvarado scoring system. Asian J Surg 36: 144-149.
7. Teixeira P G, Demetriades D (2013) Appendicitis: changing perspectives. Adv Surg 47: 119-140.
8. Poortman P, Oostvogel H J M, Bosma E, Lohle P N M, Cuesta M A, et al. (2009) Improving Diagnosis of Acute Appendicitis: Results of a Diagnostic Pathway with Standard Use of Ultrasonography Followed by Selective Use of CT. Journal of the American College of Surgeons 208: 434-441.
9. Collins G B, Fan T J, Gifford J, Tan A (2014) The accuracy of pre-appendectomy computed tomography with histopathological correlation: a clinical audit, case discussion and evaluation of the literature. Emerg Radiol 21: 589-595.
10. Rosen M P, Ding A, Blake M A, Baker M E, Cash B D, et al. (2011) ACR Appropriateness Criteria® Right Lower Quadrant Pain-Suspected Appendicitis. Journal of the American College of Radiology 8: 749-755.
11. Ahn S, group L (2014) LOCAT (low-dose computed tomography for appendicitis trial) comparing clinical outcomes following low- vs standard-dose computed tomography as the first-line imaging test in adolescents and young adults with suspected acute appendicitis: study protocol for a randomized controlled trial. Trials 15:28.
12. Miglioretti D L, Johnson E, Williams A, Greenlee R T, Weinmann S, et al. (2013) The use of computed tomography in pediatrics and the associated radiation exposure and estimated cancer risk. JAMA Pediatr 167: 700-707.
13. Wai S, Ma L, Kim E, Adekunle-Ojo A (2013) The utility of the emergency department observation unit for children with abdominal pain. Pediatr Emerg Care 29: 574-578.
14. Seo H, Lee K H, Kim H J, Kim K, Kang S-B, et al. (2009) Diagnosis of Acute Appendicitis With Sliding Slab Ray-Sum Interpretation of Low-Dose Unenhanced CT and Standard-Dose IV Contrast-Enhanced CT Scans. American Journal of Roentgenology 193: 96-105.
15. Kim S Y, Lee K H, Kim K, Kim T Y, Lee H S, et al. (2011) Acute Appendicitis in Young Adults: Low- versus Standard-Radiation-Dose Contrast-enhanced Abdominal C T for Diagnosis. Radiology 260: 437-445.
16. Keyzer C, Tack D, de Maertelaer V, Bohy P, Gevenois P A, et al. (2004) Acute Appendicitis: Comparison of Low-Dose and Standard-Dose Unenhanced Multi-Detector Row C T. Radiology 232: 164-172.
17. Huang da W, Sherman B T, Lempicki R A (2009) Systematic and integrative analysis of large gene lists using DAVID bioinformatics resources. Nat Protoc 4: 44-57.
18. Subrahmanyam Y V, Yamaga S, Prashar Y, Lee H H, Hoe N P, et al. (2001) RNA expression patterns change dramatically in human neutrophils exposed to bacteria. Blood 97: 2457-2468.
19. Kubo T, Yamashita T, Yamaguchi A, Hosokawa K, Tohyama M (2002) Analysis of genes induced in peripheral nerve after axotomy using cDNA microarrays. J Neurochem 82: 1129-1136.
20. Watson R P, Lilley E, Panesar M, Bhalay G, Langridge S, et al. (2012) Increased prokineticin 2 expression in gut inflammation: role in visceral pain and intestinal ion transport. Neurogastroenterol Motil 24: 65-75, e12.
21. Pike A F, Kramer N I, Blaauboer B J, Seinen W, Brands R (2013) A novel hypothesis for an alkaline phosphatase 'rescue' mechanism in the hepatic acute phase immune response. Biochim Biophys Acta 1832: 2044-2056.
22. Poortinga G, Wall M, Sanij E, Siwicki K, Ellul J, et al. (2011) c-MYC coordinately regulates ribosomal gene chromatin remodeling and Pol I availability during granulocyte differentiation. Nucleic Acids Res 39: 3267-3281.
23. Uemura M, Zheng Q, Koh C M, Nelson W G, Yegnasubramanian S, et al. (2012) Overexpression of ribosomal RNA in prostate cancer is common but not linked to rDNA promoter hypomethylation. Oncogene 31: 1254-1263.

24. Congiu M, Slavin J L, Desmond P V (2011) Expression of common housekeeping genes is affected by disease in human hepatitis C virus-infected liver. Liver Int 31: 386-390.
25. Derenzini M, Farabegoli F, Pession A, Novello F (1987) Spatial redistribution of ribosomal chromatin in the fibrillar centres of human circulating lymphocytes after stimulation of transcription. Exp Cell Res 170: 31-41.
26. Haaf T, Hayman D L, Schmid M (1991) Quantitative determination of rDNA transcription units in vertebrate cells. Exp Cell Res 193: 78-86.
27. Huang X, Dai F F, Gaisano Q Giglou K, Han J, et al. (2013) The identification of novel proteins that interact with the GLP-1 receptor and restrain its activity. Mol Endocrinol 27: 1550-1563.
28. Ramdass M J, Young Sing Q, Milne D, Mooteeram J, Barrow S (2015) Association between the appendix and the fecalith in adults. Can J Surg 58: 10-14.
29. Jackson H T, Mongodin E F, Davenport K P, Fraser C M, Sandier A D, et al. (2014) Culture-independent evaluation of the appendix and rectum microbiomes in children with and without appendicitis. PLoS One 9: e95414.
30. Zhong D, Brower-Sinning R, Firck B, Morowitz M J (2014) Acute appendicitis in children is associated with an abundance of bacteria from the phylum Fusobacteria. J Pediatr Surg 49: 441-446.
31. Guinane C M, Tadrous A, Fouhy F, Ryan C A, Dempsey E M, et al. (2013) Microbial composition of human appendices from patients following appendectomy. MBio 4.
32. Swidsinski A, Dorffel Y, Loening-Baucke V, Theissig F, Ruckert J C, et al. (2011) Acute appendicitis is characterised by local invasion with *Fusobacterium nucleatum/ necrophoumm*. Gut 60: 34-40.
33. Ohkusa T, Okayasu I, Ogihara T, Morita K, Ogawa M, et al. (2003) Induction of experimental ulcerative colitis by *Fusobacterium varium* isolated from colonic mucosa of patients with ulcerative colitis. Gut 52: 79-83.
34. Arit A, Bharti R, Ilves I, Hasler R, Miettinen P, et al. (2013) Characteristic changes in microbial community composition and expression of innate immune genes in acute appendicitis. Innate Immun.
35. Peyyala R, Kirakodu S S, Novak K F, Ebersole J L (2012) Oral microbial biofilm stimulation of epithelial cell responses. Cytokine 58: 65-72.
36. Zeillemaker A M, Hoynck van Papendrecht A A, Hart M H, Roos D, Verbrugh H A, et al. (1996) Peritoneal interleukin-8 in acute appendicitis. J Surg Res 62: 273-277.
37. Baines K J, Simpson J L, Wood L, Scott R, Fibbens N, et al. (2014) Sputum gene expression signature of 6 biomarkers discriminates asthma inflammatory phenotypes. J Allergy Clin Immunol 133: 997-1007.
38. Zhang Z, Harrison P, Gerstein M (2002) Identification and analysis of over 2000 ribosomal protein pseudogenes in the human genome. Genome Res 12: 1466-1482.
39. Shiue C N, Nematollahi-Mahani A, Wright A P (2014) Myc-induced anchorage of the rDNA IGS region to nucleolar matrix modulates growth-stimulated changes in higher-order rDNA architecture. Nucleic Acids Res 42: 5505-5517.
40. Remacha M, Jimenez-Diaz A, Bermejo B, Rodriguez-Gabriel M A, Guarinos E, et al. (1995) Ribosomal acidic phosphoproteins P1 and P2 are not required for cell viability but regulate the pattern of protein expression in *Saccharomyces cerevisiae*. Mol Cell Biol 15: 4754-4762.
41. D'Souza N, Karim D, Sunthareswaran R (2013) Bilirubin; a diagnostic marker for appendicitis. Int J Surg 11: 1114-1117.
42. Huckins D S, Simon H K, Copeland K, Spiro D M, Gogain J, et al. (2013) A novel biomarker panel to rule out acute appendicitis in pediatric patients with abdominal pain. Am J Emerg Med 31: 1368-1375.
43. Kaya B, Sana B, Eris C, Karabulut K, Bat O, et al. (2012) The diagnostic value of D-dimer, procalcitonin and CRP in acute appendicitis. Int J Med Sci 9: 909-915.
44. Wu J Y, Chen H C, Lee S H, Chan R C, Lee C C, et al. (2012) Diagnostic role of procalcitonin in patients with suspected appendicitis. World J Surg 36: 1744-1749.
45. Andersson M, Ruber M, Ekerfelt C, Hallgren H B, Olaison G, et al. (2014) Can new inflammatory markers improve the diagnosis of acute appendicitis? World J Surg 38: 2777-2783.

Example 2: Confirmation of Microarray Results

Figure 7:
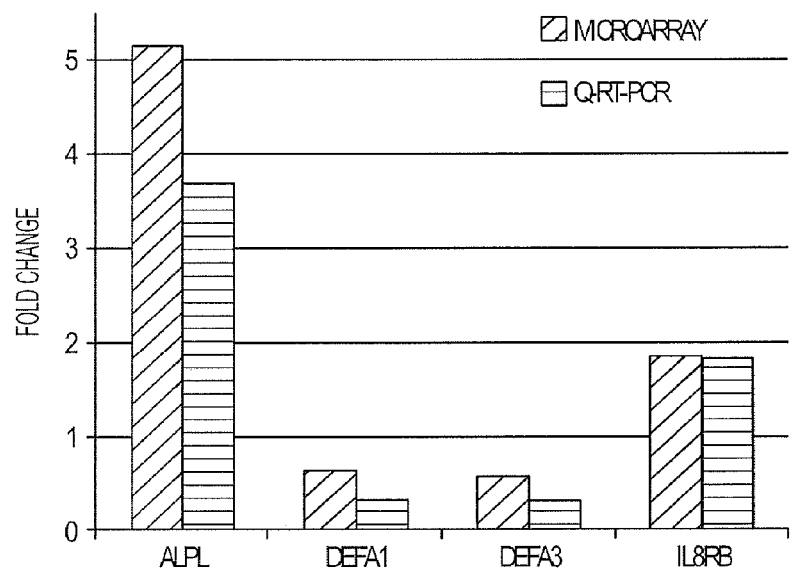
FIG. 7 shows a graph showing microarray and quantitative reverse-transcription polymerase chain reaction results for 3 genes differentially expressed in subjects with appendicitis.

Quantitative Real Time Polymerase Chain Reaction (Q-RTPCR) was sued to confirm the microarray results from Example 1. FIG. 7 shows Q-RTPCR results for 3 genes: ALPL, DEFA1/3 and IL8RB. As seen in FIG. 7, results obtained from Q-RTPCR parallel the results obtained from the microarray assays.

Methods

RNA Purification:

1.1) For validation studies, the RNA purified for microarray analysis was used. In new samples, or other embodiments, the sample of blood must be collected in an appropriate RNA stabilizer. In the present studies, Tempus tubes were used. Other stabilizers could be used, but it is possible that the specific transcripts levels of expression or their magnitude, could be different depending upon the RNA Blood tubes used and their RNA stabilizers. From the Tempus tubes, the manufacturer's instruction and reagents for column purification of RNA was used. However, technically, both DNA and RNA are purified.

2) DNAse Treatment:

2.1) To remove the DNA, which will confuse the quantitation of RNA, the sample is treated with Turbo DNA-Frve™ Kit (ThermoFisher Sci, Cat. No AM1907). We used up to 5 μg total RNA/DNA treated with 2 units/μL of TurboDNAse for 30 min at 37° C. The inactivation of DNAse was performed using the "Inactivation Reagent" (IR) provided in the kit at 0.2× volume of the total reaction, typically 20 μL of IR for 100 μL of DNase treatment. The IR contains an affinity capture reagent recognizing the TurboDNAse, thereby removing it from solution, and eluting relatively pure RNA. A variety of DNAse removal strategies are well known to anyone skilled in the art. In particular, it is common to heat-inactivate the DNAsc. While probably acceptable, it has not been specifically tested, and we cannot exclude the possibility that this would be a source of variation (SOV).

2.2) The DNase treated RNA is further purified in Qiagen RNAeasy MiniElute kit (Qiagen, Cat. No. 74204) on columns The RNA quantity is assessed by absorbance at 260 nm (NanoDrop) and the quality is assessed by the ratio of absorbance at 260 nm (RNA) to 280 nm (protein). A ratio (260/280) greater than 1.8 is desirable if measured in water, and greater than 2.0 if measured in water buffered with Tris/EDTA (TE).

3) Complementary DNA (cDNA) Synthesis:

3.1) The purified RNA was converted to cDNA using reverse transcriptase (RT) contained in the iScript cDNA Synthesis kit from Bio-Rad Laboratories (Cat. No. 170-8891). There are published reasons to believe that the type of RT enzyme could affect the efficiency of cDNA synthesis, and therefore, the measured levels of specific transcripts by qRT-PCR. In particular, the presence or absence of the RNAse H activity in the RT enzyme might be a relevant SOV. The iScript cDNA kit reverse transcriptase contains RNase H enzymes for degradation of RNA template in the amplification process.

4) PCR Probe Selection:

4.1) Sense and antisense probes for PCR were selected using the cDNA sequences extracted from Genbank accession numbers disclosed in Table 1. The cDNA sequences were analyzed by Geneious software to identify primers with matching melting temperatures (Tm) of 60° C. under standard RT-PCR conditions. The primers identified and used are shown in Table 1.

4.2) In this example, 6 transcripts were targeted for qRT-PCR quantitation. Four of these transcripts (ALPL, DEFA1, DEFA3, IL8RB) were selected from the 16 g and 37 g lists of DEGs that are diagnostic of appendicitis. Two other transcripts, ACTB and SpiB, were used as transcripts which should not vary according to appendicitis status, and thus are considered 'invariant' for this example.

4.3) For each transcript-specific reaction, additional samples are prepared in which the pooled control cDNA (Con) is used at higher, and lower quantities, typically in 10-fold steps, to create a standard dose-response curve for each primer pair. This curve confirms that the qPCR is able to detect higher and lower transcript levels, and is used to convert the Ct to a relative abundance measure as described below.

5) qRT-PCR Conditions:

5.1) A standard amount of cDNA (0.20-0.25 ng) from the patient samples, or a pooled control sample (Con), was combined with a fixed amount of the transcript-specific primer pairs (1.25 µM) and a master mix SSOAdvanced™ Universal SYBRO® Green Supermix (Bio-Rad, Cat. No.: 172-5274) containing a mix of antibody-mediated hot-start Sso7d fusion polymerase, dNTPs, MgCl2, enhancers, stabilizers, a blend of passive reference dyes (including ROX and fluorescein) and SYBR Green fluorescent dye, which reports the level of PCR amplimer that is present after each amplification cycle. There are numerous acceptable ways to quantitate PCR amplimer levels, including, but not limited to, SYBR Green, EVA green, and fluorescently-labeled internal probes commonly referred to TaqMan probes. Another envisioned embodiment of the invention would be to quantitate the transcript levels using droplet digital PCR (ddPCR, BioRad) or hybrid-based transcript counting methods, such as Nanostring.

In this example, we employed the BioRad SSOAdvanced kit reagents. Each transcript-specific primer pair and sample, cDNA was analyzed in a separate well of a 384-well plate in duplicate for each primer pair. Thus, for a given patient sample, 12 qPCR reactions were performed (6 primer pairs, each in duplicate). The mixture containing probes, cDNA sample, and PCR reagents, including fluorescent dye, in a final volume of 14 µl, were loaded using the automatic liquid handler (Eppendorf, epMotion® 5770) subjected to thermocycling as described below.

5.2) The mixture of these reagents was incubated in a BioRad CFX384™ Real-Time System with C1000™ thermocycler using a temperature program of: 2 min at 98° C., followed by 45 amplification cycles of 5 see at 98° C., and 10 see @ 60° C., finalized with 10 sec @ 75° C. and 4 sec @ 95° C. dissociation stage. After each cycle, the level of fluorescence of the SYBR Green dye bound to dsDNA amplimers was quantified by stimulation with appropriate filters for excitation and emission. The reaction was cycled 40 times and then held at 4° C. after the last cycle.

6) Data Analysis:

6.1) The real-time quantitative PCR instruments measure fluorescence generated by the amplimer/dye complex after each cycle of amplification. Because the amounts of primers and free nucleic acids are limiting, these reaction reach a saturated maximum of fluorescence typically prior to 40 cycles of amplification. The number of cycles observed to reach half-maximal fluorescent intensity is said to be a Cycle Threshold (Ct) of Cycle Quantity (Cq) which is inversely correlated to the amount of transcript cDNA in the reaction. Thus, the higher the level of target cDNA present, the fewer cycles will be needed to reach a given Ct. In practice, there are numerous acceptable methods to stipulate the Ct based on the fluorescence curve, and as long as the Ct is applied uniformly to the samples in each transcript-specific reaction, including the Con samples, then the results should be informative for the present purposes.

6.2) The Ct values for each reaction are converted to a relative abundance (RA) of the transcript by interpolation to the standard curve for each primer pair. That RA level per duplicate PCR tube is then averaged for the 2 duplicates, and then adjusted by the abundance of the 'invariant' transcript levels. A very large number of invariant transcripts would be acceptable, and some that are commonly used by those skilled in the art include: glyceraldehyde 3-phosphate dehydrogenase (GAPDH), β-actin (ACTB), hypozanthine phosphoribosyltransferase 1 (HPRT), and 18S ribosomal RNA. In the present invention, it was empirically determined that ACTB provided efficient normalization, but the invention is not constrained by the method of normalization.

6.3) The RA levels of the 4 diagnostic transcripts were combined in the following way to predict the outcome of appendicitis:

6.3.1) To account for arbitrary nature of RA value, it was normalized to a percentile of the mean value in the entire run of 36 samples, yielding a % RA value, where 1.00 would be equal to the mean value of that transcript target.

6.3.2) Using the % RA value, the diagnostic goal is to determine whether the ALPL and IL8RB levels are increased disproportionately to the DEFA1 levels. In principle, DEFA3 levels could be used, or a combination of DEFA1 and DEFA3 levels, but for simplicity DEFA1 levels were found to be adequate. Thus, the ratio of % RA of ALPL (% ALPL) to % RA of DEFA1 (% DEFA1), and the ratio of % RA of IL8RB (% IL8RB) to % DEFA1 were computed to yield % ALPL/% DEFA1 and % IL8RB/% DEFA1. Those two values were averaged to compute the App Score. In this series of 36 patient samples, the App Score had a range of 0.04-44.7.

Thus, to summarize,

App Score=[(% ALPL/% DEFA1)+(% *IL8RB*/% DEFA1)]/2

Another construction is App Score=[(% ALPL+% *IL8RB*)/2]/% DEFA1

6.3.3) On both logical grounds, and empirical observation, if the App Score is >1 then the normalized ALPL and IL8RB levels are higher than DEFA1 levels and this is taken as diagnostic of an increased likelihood of appendicitis. In actual practice, there would be numerous mathematical and technical means to arrive at a similar assessment of the relative levels of these predictive transcripts identified in the 16 g or 37 g lists.

6.3.4) To test the diagnostic ability of the App Score, it was converted to a scale of 1-10 which is a common metric range used in the Receiver-Operator Characteristic (ROC) statistic. The conversion from App Score to App Level (1-10) was achieved with the following conversion table:

TABLE 6

Conversion Table for converting App Score to App Level

| Coding Key App Score | App Level |
|---|---|
| <0.2 | 1 |
| <0.4 | 2 |
| <0.6 | 3 |
| <0.8 | 4 |
| <1.0 | 5 |
| <2 | 6 |
| <4 | 7 |
| <8 | 8 |
| <16 | 9 |
| >16 | 10 |

Figure 8:
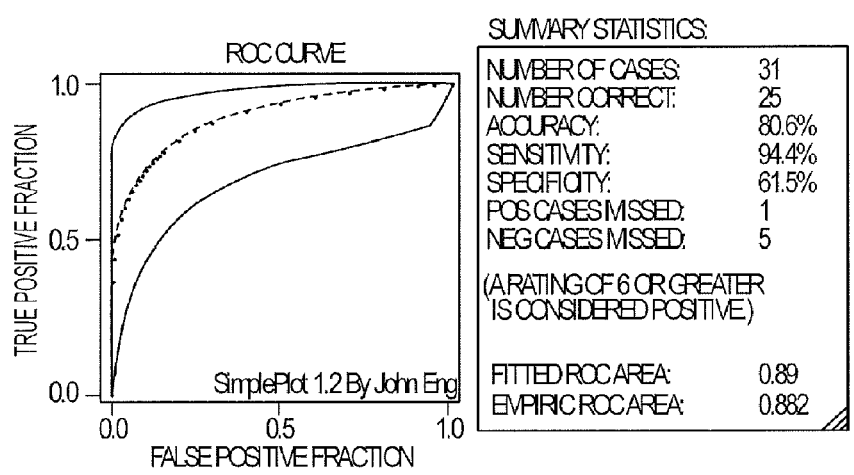
FIG. 8 shows a Receiving Operating Characteristic (ROC) curve with data from 3 gene transcripts.

As discussed above, a predictive test was built taking the data from FIG. 10. A very simple way to predict Appendicitis (Appy) using only 3 gene transcripts (IL8RB, DEFA1, ALPL) and one control transcript (Actin) was developed. FIG. 8 shows a graph of the ROC curve with sensitivity and specificity. In practice, the test gives a score from 1 to 10, where 5-6 is about a 50% risk of Appy, and a score above 7 indicates likely Appy.

The true presence or absence of appendicitis was known from clinical analysis and was scored as a binary variable where 0=absent, 1=appendicitis. Five of the 36 patients were excluded from analysis because they had a clinical diagnoses of lower respiratory infection, which is unrelated to the present invention. An App Score>1, which is an App Level of 6 or greater, was used as a threshold for predicted appendicitis. The predicted outcome (App Level) and the true outcome were used to compute a 'confusion table' and an ROC curve by the method of John Eng: (JROCFIT: Johns Hopkins University, Baltimore, MD Version 1.0.2, March 2004. URL: http://www.rad.ihmi.edu/jena/javarad/roc/JROCFITi.html).

The results are shown in FIG. 8, and indicate that overall the accuracy was 80.6%, with 94.4% sensitivity in detecting clinically diagnosed appendicitis.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of treating a human subject diagnosed with appendicitis comprising administering an antibiotic to the subject, removing the appendix of the subject, or a combination thereof, wherein the human subject is diagnosed by a method comprising:
obtaining a biological sample from said subject;
detecting expression levels of at least three or more biomarkers in the biological sample selected from the group consisting of Chemokine C-X-C receptor 1, Interleukin 8 receptor β, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; and
diagnosing the subject with appendicitis when at least three or more of said biomarkers are differentially expressed compared to the expression levels of said biomarkers in a group of human subjects not suffering from appendicitis.

2. The method of claim 1, wherein said biological sample is a blood sample, serum sample, or a plasma sample.

3. The method of claim 1, wherein said at least three biomarkers are selected from the list consisting of Interleukin 8 receptor β, Defensin alpha 1, Defensin alpha 1B, Defensin alpha 3 and Alkaline phosphatase.

4. The method of claim 1, further comprising determining the ratio of expression between Alkaline phosphatase or Interleukin 8 receptor β and Defensin alpha 1, Defensin alpha 1B or Defensin alpha 3 and comparing said ratio to a control sample, wherein an increase in the ratio of expression is indicative of appendicitis.

5. The method of claim 1, wherein detecting expression levels of at least three or more biomarkers comprises measuring RNA levels of said at least three or more biomarkers.

6. The method of claim 5, wherein measuring RNA levels comprises using reverse transcriptase and polymerase chain reaction.

7. The method of claim 5, wherein measuring RNA levels comprises using microarray analysis.

8. The method of claim 5, wherein measuring RNA levels comprises using RNA sequencing.

9. The method of claim 1, wherein comparing the expression levels of said at least three or more biomarkers comprises using a prediction model to determine if a pattern of expression of said at least three or more biomarkers is indicative of appendicitis.

10. The method of claim 5, wherein said at least three RNA sequences are selected from the group consisting of LOC100129902, LOC100131205, LOC100131905, LOC100132291, LOC100132394, LOC100132742, LOC100134364, LOC391370, LOC646785, LOC644191 and C5orf32.

11. The method of claim 1, further comprising performing a computed tomography (CT) scan, a magnetic resonance imaging (MRI) scan, an ultrasound sonography, or any combination thereof on said subject prior to treating said subject for appendicitis.

12. The method of claim 5, wherein said three RNA sequences are Interleukin 8 receptor β, Defensin alpha 1, and Alkaline phosphatase.

13. A method of treating a human subject diagnosed with appendicitis comprising administering an antibiotic to the subject, removing the appendix of the subject, or a combination thereof, wherein the human subject is diagnosed by a method comprising:
obtaining a biological sample from said subject;
detecting the expression level of Defensin alpha 3; and diagnosing the subject with appendicitis when the Defensin alpha 3 is differentially expressed compared to the expression level of Defensin alpha 3 in a group of human subjects not suffering from appendicitis.

14. The method of claim 13, wherein detecting the expression level comprises measuring RNA level of Defensin alpha 3.

15. The method of claim 14, wherein measuring RNA levels comprises using reverse transcriptase and polymerase chain reaction.

16. The method of claim 14, wherein measuring RNA levels comprises using microarray analysis.

17. The method of claim 14, wherein measuring RNA levels comprises using RNA sequencing.

* * * * *